United States Patent [19]

Michaels et al.

[11] Patent Number: 5,055,397

[45] Date of Patent: Oct. 8, 1991

[54] GEOMICROBIOLOGICAL METHODS OF ORE AND PETROLEUM EXPLORATION

[75] Inventors: Glenda B. Michaels, Gunnison, Colo.; Walter C. Riese, Richmond, Tex.

[73] Assignee: Atlantic Richfield Company, Los Angeles, Calif.

[21] Appl. No.: 134,431

[22] Filed: Dec. 17, 1987

[51] Int. Cl.$^5$ .............................................. C12Q 1/64
[52] U.S. Cl. .......................................... 435/9; 435/6; 435/34; 435/35; 435/8
[58] Field of Search ....................... 435/6, 9, 34, 35, 8, 435/264, 281

[56] References Cited

U.S. PATENT DOCUMENTS

| | | | |
|---|---|---|---|
| 2,269,889 | 1/1942 | Blau | 435/9 |
| 2,921,003 | 1/1960 | Rosenfeld | 435/9 |
| 4,421,848 | 12/1983 | Whitlock | 435/34 |

FOREIGN PATENT DOCUMENTS 676970 12/1963 Canada .................................... 435/9

OTHER PUBLICATIONS

Glenda B. Michaels, Walter C. Riese, *Microbiological Exploration for Mineral Deposits: A New Technique*, Applied Geochemistry, Mar. 16, 1986, vol. 1, pp. 103–109.

Glenda B. Michaels, Walter C. Riese, *Luminometry and Isotropy in Microbiological Exploration for Mineral Deposits*, Applied Geochemistry, Jan. 15, 1987, vol. 1(5), pp. 559–565.

Albright, L. J., Wentworth, J. W., and Wilson, E. M. (1972) Technique for Measuring Metallic Salt Effects Upon the Indigenous Heterotrophic Microflora of a Natural Water, Sater Res. 6, 1589–1596.

Babich, H., and Stotzky, G. (1980) Environmental Factors that Influence the Toxicity of Heavy Metal and Gaseous Pollutants to Microorganisms, Crit. Rev. Microbiol. 8, 99–146.

Bell, C. R., Holder-Franklin, M. S., and Franklin, M. (1980) Heterotrophic Bacteria in Two Canadian Rivers, I. Seasonal Variations in the Predominant Bacterial Populations, Water Res. 14, 449–460.

Bopp, L. H., Chakrabarty, A. M., and Ehrlich, H. L. (1983) Chromate Resistance Plasmid in *Pseudomonas fluorescens*, J. Bacteriol. 155, 1105–1109.

Chen, C-M., Mobley, H. L. T., and Rosen, B. P. (1985) Separate Resistances to Arsenate and Arsenite (Antimonate) Encoded by the Arsenical Resistance Operon of R Factor R773, J. Bacteriol. 161, 758–763.

Costerton, J. W., and Irvin, R. T. (1981) The Bacterial Glycocalyx in Nature and Disease, Ann. Rev. Microbiol. 35, 299–324.

Crawford, R. D., and Worcester, P. G. (1916) Geology and Ore Deposits of the Gold Brick District, Colorado, Colo. Geol. Survey Bull. 10.

El-Shaarawi, A. H., Esterby, S. R., and Dutka, B. J. (1981) Bacterial Density in Water Determined by Poisson or Negative Binomial Distributions, Appl. Environ. Microbiol. 41, 107–116.

(List continued on next page.)

*Primary Examiner*—Sam Rosen
*Attorney, Agent, or Firm*—Jacques M. Dulin

[57] ABSTRACT

Geomicrobiological exploration method employing one or more culture, luminometry or tritiated thymidine assays of microbes (bacteria) for sensitivity, determined as survival rate in percentage, of the microbes to selected toxic materials, preferably heavy metals and/or hydrocarbons. The survival assay values are plotted as contours on a geophysical map and target areas of potential interest are identified and further evaluated by inspection or other techniques. Examples show actual use of the techniques to identify a target area in a raw prospect petroleum lease area which was drilled to successful oil discovery thus proving the method. Sensitivity test incubation ranges from 1–3 hours (preferably 2 hours) for heavy metals at 20–25 degrees C., and 3–10 min. for pentene/hexane at 15–20 degrees C. Luminometry is fastest, being run in 1.5–30 minutes and most suitable for field surveys. Toxics concentrations may range from 0.001 ug/ml to 15,000 ug/ml for heavy metals to 0.001–25 vol % for hydrocarbons.

20 Claims, 20 Drawing Sheets

OTHER PUBLICATIONS

Foster, T. J. (1983) Plasmid-Determined Resistance to Anti-Microbial Drugs and Toxic Metal Ions in Bacteria, Microbiol. Rev. 47, 361–409.

Fry, J. C., and Zia, T. (1982) Viability of Heterotrophic Bacteria in Freshwater, J. Gen. Microbiol. 128, 2841–2850.

Fuhrman, J. A., and Azam, E. (1982), Thymidine Incorporation as a Measure of Heterotrophic Bacterioplankton Production in Marine Surface Waters: Evaluation and Field Results, Mar. Biol. 66, 109–120.

Gadd, G. M., and Griffiths, A. J. (1978) Microorganisms and Heavy Metal Toxicity, Microb. Ecol. 4, 303–317.

Goulder, R. (1980) Seasonal Variations in Heterotrophic Activity and Population Density of Planktonic Bacteria in a Clean River, J. Ecoi. 68, 349–363.

Haack, T. K., and McFeters, G. A. (1982) Microbial Dynamics of an Epilithic Mat Community in a High Alpine Stream, Appl. Environ. Microbiol. 43, 702–707.

Haefeli, C., Franklin, C., and Hardy, K. (1984) Plasmid Determined Silver Resistance in *Pseudomonas stutzeri* Isolated from a Silver Mine, J. Bacteriol. 158, 389–392.

Houba, C., and Remacle, J. (1980) Composition of the Saprophytic Bacterial Communities in Freshwater Systems Contaminated by Heavy Metals, Microb. Ecol. 6, 55–69.

Jardim, W. F., and Pearson, H. W. (1985) Copper Toxicity to Cyanobacteria and Its Dependence on Extracellular Ligand Concentration and Degradation, Microb. Ecol. 11, 139–148.

Jonas, R. B., Gilmour, C. C., Stoner, D. L., Weir, M. M., and Tuttle, J. H. (1984) Comparison of Methods to Measure Acute Metal and Organometal Toxicity to Natural Aquatic Microbial Communities, Appl. Environ. Microbiol. 47, 1005–1011.

Jones, J. G. (1972) Studies on Freshwater Bacteria: Association with Algae and Alkaline Phosphatase Activity, J. Ecol. 60, 59–75.

Jones, J. G., and Simon, B. M. (1980) Variability in Microbiological Data from a Stratified Eutrophic Lake, J. Appl. Bacteriol. 49, 127–135.

Karl, D. M. (1980) Cellular Nucleotide Measurements and Applications in Microbial Ecology, Microbiol. Rev. 44, 739–796.

Karl, D. M., and Craven, D. B. (1980) Effects of Alkaline Phosphatase Activity on Nucleotide Measurements in Aquatic Microbial Communities, Appl. Environ. Microbiol. 41, 549–561.

Klein, D. A., and Wu, S. (1974) Stress: A Factor to be Considered in Heterotrophic Microorganism Enumeration from Aquatic Environments, Appl. Microbiol. 27, 429–431.

Kosinski, R. J., Singleton, F. L., and Foster, B. G. (1979) Sampling Culturable Heterotrophs from Microcosms: A Statistical Analysis, Appl. Environ. Microbiol. 39, 906–910.

Laegreid, M., Alstad, J., Klaveness, D., and Seip, H. M. (1983) Seasonal Variation of Cadmium Toxicity Toward the Alga *Selenastrum capricornutum* Printz in Two Lakes with Different Humus Content, Environ. Sci. Technol. 17, 357–361.

Reichardt, W., Overbeck, J., and Steubing, L. (1967) Free Dissolved Enzymes in Lake Waters, Nature 216, 1345–1347.

Robinson, J. B., and O. H. Tuovinen, 1984, Mechanisms of Microbial Resistance and Detoxification of Mercury and Organomercurial Compounds: Physiological, Biochemical, and Genetic Analyses, Microbiol. Rev. 48, 95–148.

Silver, S. (1981) Mechanisms of Plasmid-Determined Heavy Metal Resistances, In *Molecular Biology, Pathogenicity, and Ecology of Bacterial Plasmids* (eds. S. B. Levy, R. C. Clowes and E. L. Koenig), Plenum Press.

Sjogren, E. E., and Port, J. (1981) Heavy Metal-Antibiotic Resistant Bacteria in a Lake Recreational Area, Water Air Soil Pollut. 15, 29–44.

Summers, A. O. (1984) Genetic Adaptations Involving Heavy Metals, In *Current Perspectives in Microbial Ecology* (Eds. M. J. Klug and C. A. Reddy), American Society for Microbiology.

Timoney, J. F., Port, J. Giles, J., and Spanier, J. (1978) Heavy-Metal and Antibiotic Resistance in the Bacterial Flora of Sediments of New York Bight, Appl. Environ. Microbiol. 36, 465–472.

Updegraft, D. M., (1986) Geomicrobiological Prospecting: Past and Future, In Mineral Exploration: Biological Systems and Organic Matter (eds. D. Carlisle et al.), Prentis Hall.

Varma, M. M., Thomas, W. A., and Prasad, C. (1976) Resistance to Inorganic Salts and Antibiotics Among Sewage-Borne Enterbacteriaceae and Achromobacteriaceae, J. Appl. Bacteriol. 41, 347–349.

Dings, McC. G., and Robinson, C. S. (1957) *Geology and Ore Deposits of the Garfield Quadrangle, Colorado,* U.S. Geol. Survey Prof. Pap. 289.

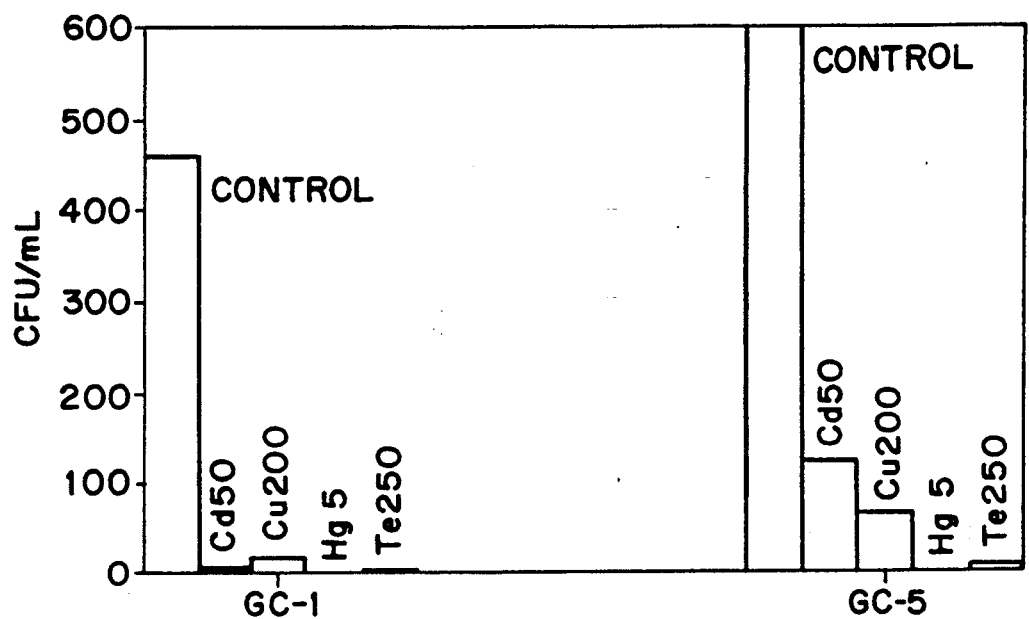
Fig_1
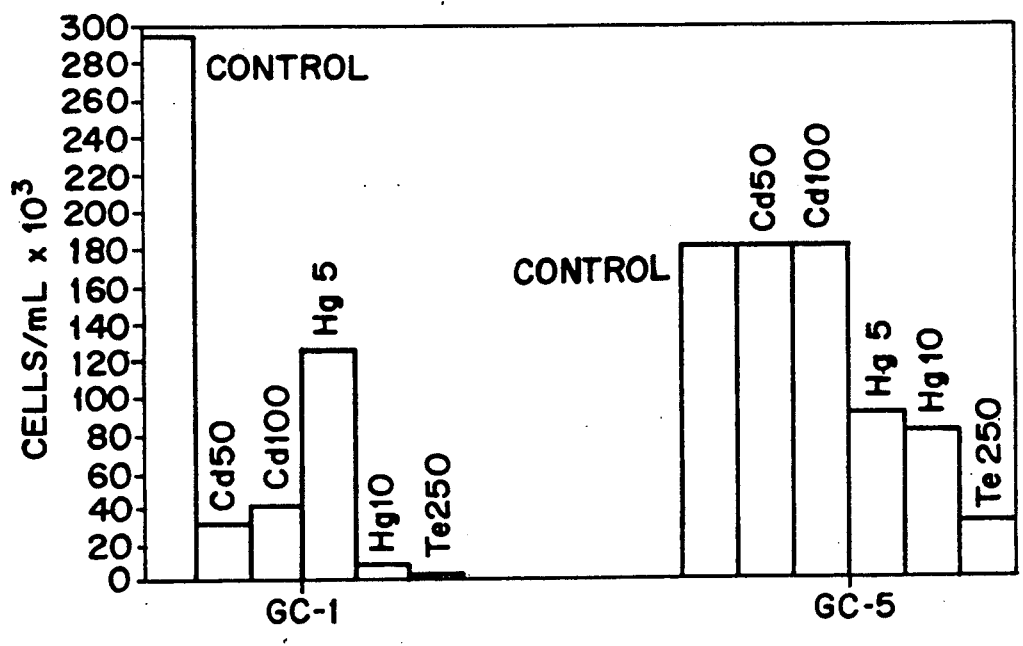
Fig_2

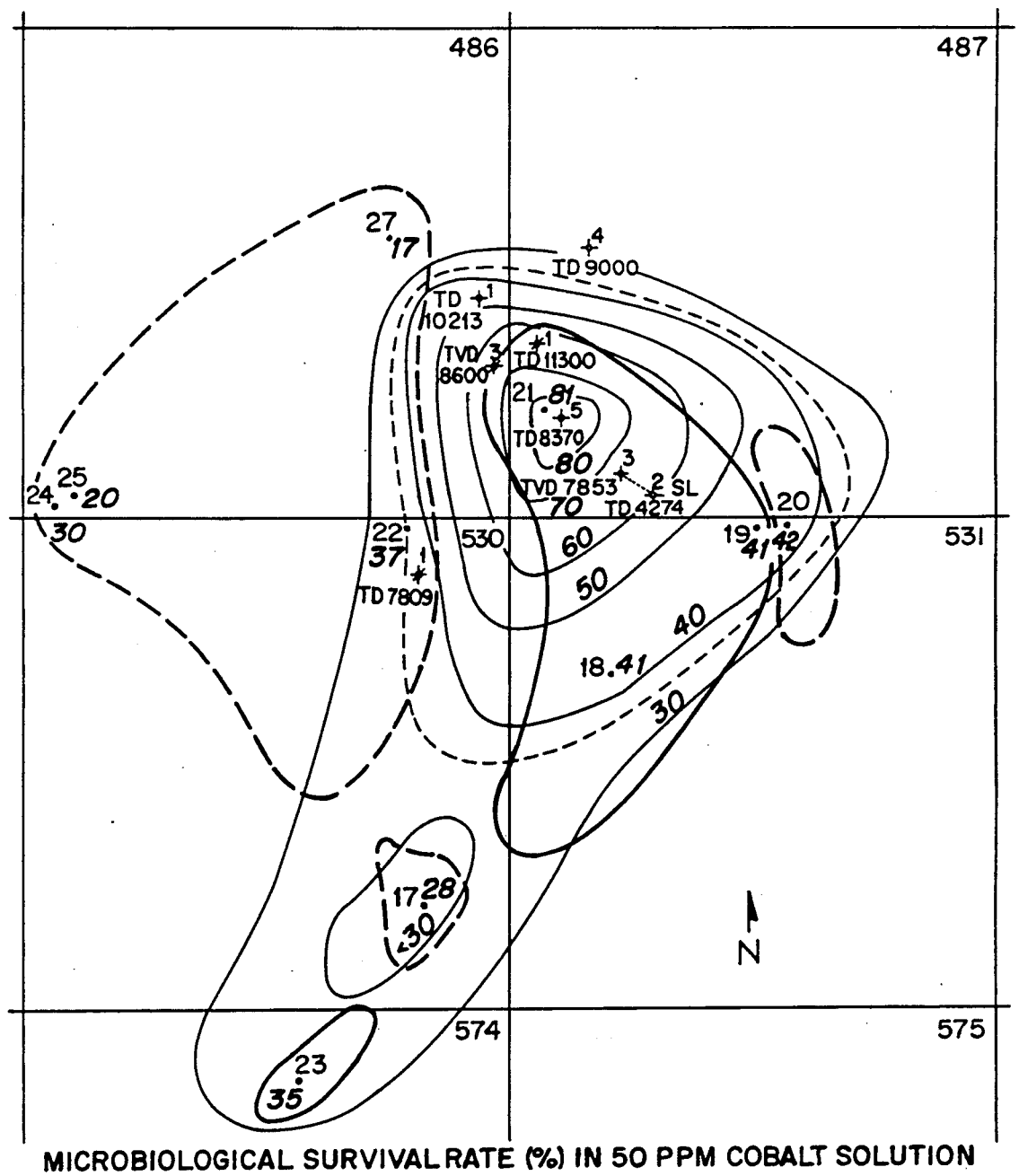
MICROBIOLOGICAL SURVIVAL RATE (%) IN 50 PPM COBALT SOLUTION
Fig_3

MICROBIAL SURVIVAL RATE (%) IN 100 PPM COBALT SOLUTION

MICROBIAL SURVIVAL RATE (%) IN 10 PPM NICKEL SOLUTION

MICROBIOLOGICAL SURVIVAL RATE (%) IN 20 PPM NICKEL SOLUTION

MICROBIAL SURVIVAL RATE (%) IN PENTANE SOLUTION

MICROBIAL SURVIVAL RATE (%) IN HEXANE SOLUTION

VANADIUM CONTENT (TOTAL DIGESTION) PPM

NICKEL CONTENT (TOTAL DIGESTION) PPM

ZINC CONCENTRATION (TOTAL DIGESTION) PPM

MICROBIAL SURVIVAL RATE (%) IN 50 PPM COBALT SOLUTION

MICROBIAL SURVIVAL RATE (%) IN 100 PPM COBALT SOLUTION

MICROBIAL SURVIVAL RATE (%) IN 10 PPM NICKEL SOLUTION

MICROBIAL SURVIVAL RATE (%) IN 20 PPM NICKEL SOLUTION

MICROBIAL SURVIVAL RATE (%) IN 20 PPM ZINC SOLUTION

MICROBIAL SURVIVAL RATE (%) IN PENTANE SOLUTION
(4 MINUTES EXPOSURE)

MICROBIAL SURVIVAL RATE (%) IN HEXANE SOLUTION
(4 MINUTES EXPOSURE)

VANADIUM CONCENTRATION (TOTAL DIGESTION) PPM

NICKEL CONCENTRATION (TOTAL DIGESTION) PPM

ZINC CONCENTRATION (TOTAL DIGESTION) PPM

GEOMICROBIOLOGICAL METHODS OF ORE AND PETROLEUM EXPLORATION

FIELD

This Application relates to improved methods of prospecting for ores and petroleum, more particularly to methods of prospecting for heavy metal-bearing ores and petroleum employing luminometry and tritriated thymidine assays of microbes (bacteria) for sensitivity, determined as survival rate in percentage, of the microbes to selected toxic materials, preferably heavy metals and/or hydrocarbons. The methods of this Application are suitable for heavy metal, and metal-bearing ore prospecting and oil exploration, particularly sub-sea exploration.

BACKGROUND

Geochemical exploration for mineral resources typically relies on the collection of soils, sediments, or rocks and the subsequent analysis of these media for the element being sought or its pathfinders. Michaels and Riese (1986) suggested that micro-organisms, especially bacteria, should also be considered as exploration tools. Like other organisms, bacteria are sensitive to the toxic effects of heavy metals in their environment. Unlike many organisms, however, bacteria possess genetic mechanisms which allow them to adapt relatively rapidly to the presence of these metals and thereby survive and thrive in their presence (Bopp et al., 1983; Chen et al., 1985; Foster, 1983; Haefeli et al., 1984; Robinson and Touvinen, 1984; Silver, 1981; Summers, 1984). Measurement of this genetically encoded resistance can be accomplished via culture techniques which were also outlined by Michaels and Riese (1986). If the metals exerting the selection pressure requiring resistance to develop are supplied to the environment by a slowly weathering ore deposit or alteration halo, the presence of resistant bacteria may then be used as an indicator of that deposit.

While the use of microorganisms as a prospecting tool will realize a significant saving in both time and money if culture "assay" methods are employed as compared to conventional geochemical methods, culture assay methods require 5-7 days of incubation time as well as facilities for media preparation and the disposal of cultures. Culture assays are also particularly unsuited for field exploration, particularly in rugged country where seasonal access in very short. Further, as pointed out in Michaels and Riese (1986) cultures must not be incubated at temperatures above 20 degrees centigrade if the bacteria's natural environment does not exceed that temperature. Thus, the time involved to hike back out to sophisticated laboratory facilities might be sufficiently long that the bacteria collected in the samples may increase, thus distorting results or rendering the results so suspect as to be worthless. Even more importantly, the lag in obtaining assay results may mean that rapid follow-up in the field is impossible as the field crew may have moved on, and may not be able to return to the area until a year later if the prospecting season has closed or the crews are scheduled elsewhere.

Attempts to date to utilize microbes in petroleum exploration programs have relied on the detection of microbes specifically adapted to utilization of methane as a food source. The assumption is made that hydrocarbon reservoirs leak, that these escaped hydrocarbons make their way to the surface (seafloor) in some way, and are there utilized by the resident microbial community as a food source. Hydrocarbons may also represent a toxic substance to bacteria, however, and the resident microbial community may adapt to these in a manner similar to that described for metals.

Accordingly, there is a need for a fast, field manageable assay that employs the principal of microorganism sensitivity to the toxic effects of heavy metals and/or hydrocarbons in their environment, either directly as a mapping tool for such heavy metals, or as pathfinders for other metals or petroleum.

THE INVENTION

Objects

It is among the objects of this invention to provide improved methods of assay of the quantities of microorganisms, particularly bacteria, having resistance to heavy metals and/or hydrocarbons in both land and sub-sea environments.

It is another object of this invention to employ luminometry as a fast technique for assaying microbial populations sensitive to heavy metals and/or hydrocarbons.

It is another object of this invention to provide an isotopic method of assay of microorganisms sensitive to heavy metals and/or hydrocarbons in their environment.

It is another object of this invention to provide methods for mapping of heavy metals and hydrocarbon sensitivity of microorganisms in both land and sub-sea environments as indicative of the presence of such metals, other metals or metalbearing ores and petroleum.

Still further objects of this invention will be evident from the description which follows.

SUMMARY

The invention comprises the use of specially adapted luminometry and isotopy techniques to assay the populations of toxic materials-resistant bacteria obtained in land and sub-sea environments as indicative of the presence of either high quantities of the "toxics" themselves or as pathfinders for other metals and petroleum. The toxic materials of particular interest herein are heavy metals and/or hydrocarbons, although the methods of this invention are adaptable to other toxics and/or toxins. A "pathfinder" is a heavy metal that is commonly associated with another mineral of interest or hydrocarbon such as petroleum. For example, tellurium, arsenic, mercury and cadmium are common pathfinders for gold. On the other hand, zinc is its own pathfinder. Which metals are pathfinders depends in part on the specifics of a particular geological area and can be independently corroborated by mineral sampling and conventional wet assay techniques.

In the case of petroleum hydrocarbons, we have surprisingly found that heavy metals act as pathfinders for petroleum. Thus, our methods look for genetically encoded tolerance of the whole bacterial population in the particular ecosystem. By plotting the location of samples showing common heavy metal or hydrocarbon tolerances, we can develop heavy metal concentration contour maps, analogous to topographic contour maps, which help point to localized concentrations of minerals or petroleum.

The basic method of this invention is a three step procedure of which each step has a number of sub-steps. In the first step, appropriate samples for microbiological analysis are obtained from the ecosystem and their location recorded. In the case of exploration on dry land, we prefer grab samples which represent the B-soil horizon or water column. In the case of undersea exploration, we prefer sediment samples obtained below a depth of about 0.5 meters, preferably about 1 meter below the surface of the seabed to ensure that the microbial population is not contaminated by the presence of sulfates. The sample is then divided into a number of aliquots, at least one being used as a control in media having substantially no metal ion concentration. Where the ambient microbial content is low, the bacteria can be concentrated by filtration from the sample. Other aliquot(s) are put into one or more test solution(s) containing various levels of metal or hydrocarbon concentrations. Depending on the concentration, various percentages of the microbes survive after incubation for from 3-10 minutes for hydrocarbons and 1-3 hours for heavy metals. Incubation may be at 20-25 degrees C. unless the ecosystem is normally colder than that, e.g. above 3000 meters, or seabed sediments, in which case incubation may be in the range of from about 5 degrees C. to below 20 degrees C.

For petroleum prospecting, we also include aliquots for testing for cell membrane adaptations to hydrocarbons present in the environment. We have found that bacteria have genetically adapted to hydrocarbons present in their environment so that they can tolerate various levels of hydrocarbons. We employ a microbial survival test, employing gaseous or liquid hydrocarbons as the toxic screening substance. While the hydrocarbons can range from $C_1$-$C_{33}$ compounds, we prefer $C_1$-$C_{14}$ hydrocarbons. Most preferred are liquid hydrocarbons, such as pentane, hexane, mixtures or combinations thereof. The quantity of surviving microbes is then assayed in Step 2 below.

In Step 2, the microbes that survive the microbiological screening test of Step 1 are then subjected to luminometry or isotopy procedures to quantitatively determine the population of surviving microbes at the particular heavy metal or hydrocarbon concentration(s). In the case of copper, the bacterial population surviving must be removed from the copper ion incubation mixture by membrane filtration and resuspended into distilled water for the assay, as copper is an enzyme poison that interferes with the assay.

In Step 3, the assay concentrations corresponding to sample locations are then mapped against a known geographical or topographical map so that the outlines of metal concentration contours can be plotted. It should be understood that this step is optional, as the assay may not be part or an overall field assay, but rather may be for metal concentration or hydrocarbon tolerance at a single particular location. Where the metal concentrations are those of pathfinder metal(s), the values for the heavy metal concentrations can then be translated to those of the indicated ore or petroleum hydrocarbon, if desired. As the luminometry assays can be ascertained within a period on the order of 1.5 to 30 minutes, where the values indicate, additional environmental grab or sediment sampling can be immediately taken in order to, fill in, complete or interpolate the prior results. Thus, relatively immediate focus and trends can be ascertained while still in the field.

The luminometry or isotopy method may be used alone. The isotopy method is more suitable for laboratory operation as it requires a liquid scintillation counter. Thus, the isotopy method may be more useful for marine prospecting as the survey ship would be more likely to have room and support facilities for such counter as compared to land based field operations.

The approach to geomicrobiological exploration of this invention involves two points which the prior art methods of assaying microbes based on methane as a food source ignores: 1) hydrocarbons (oils) often have heavy metals chelated to them, most notably V and Ni, which metals constitute toxins in many microbial communities; and 2) hydrocarbons themselves may act as solvents to cell membranes, thereby destroying any microbial community they contact.

The leakage of hydrocarbons to the surface represents an environmental stress to which resident microbial communities must adapt or be destroyed. This adaption takes place for microbial communities which reside in areas of hyrocarbon seeps. On the basis of research reported in the literature, such hydrocarbon and/or toxic metal resistance adaptation takes place via genetic mutation or transfer of secondary replicon structures called plasmids.

The exploration technique of this invention involves detecting the pervasiveness of this genetically-encoded tolerance in the total microbial community present in surface samples (water, soil, or marine sediment). Sub-surface sediment samples are collected (offshore) with piston-coring devices and a split is taken one meter down from the seafloor surface. This sample is analyzed to determine how extensive (numerous) the resident population is. The sample is then inoculated with an elevated concentration of the toxin (metal, hydrocarbon) being used as a pathfinder and the percentage of the population which survives is determined via the use of luminometry and/or isotopy.

The method of this invention has preceeded from confirmatory sampling conducted over known hydrocarbon accumulations (MC 486-531) to surveys over raw prospects. Pre-drill predictions have been made (MC 665-710) and proven successful in subsequent drilling.

Our work indicates that bacteria in the subsea areas we have studied for presence of oil have developed tolerance to Co, Ni, and Zn. Other trace elements known to be associated with oils include B, Cr, Cu, F, Fe, Mn, Mo, Se, Sn, V, As, Hg, Cd, Pb, U, Be, Br, Ga, Ba, Ge, Sb, Re, Al, Ti, Sr, Ag, Au, and Rb. Any or all of these may prove to be useful pathfinders in the context of the exploration technique we have developed. Of these other trace elements, Cr, Sn, V, Cd, Ag, Au, Ti, and U are the most preferred as tolerance sensitivity test metals.

Our work also indicates that bacteria in the subsea areas we have studied for presence of oil have developed tolerance to hydrocarbons such as pentane and hexane. Naturally occurring hydrocarbon accumulations suitable for economic development may contain hydrocarbons that vary in composition from $C_1$ to $C_{33}$ or larger. Bacterial populations may develop tolerances to any of these compounds, or any combination of these compounds. We prefer compounds in the range of $C_1$ through $C_{14}$ as tolerance sensitivity test hydrocarbons as pathfinders for oil in the context of the exploration techniques of this invention.

BRIEF DESCRIPTION OF THE DRAWINGS

The principles of the invention are illustrated by reference to the drawings in which:

FIG. 1 is a bar graph showing levels of bacteria tolerant to heavy metals in a dry land exploration area as determined by the relatively slow (5-7 days) culture method;

FIG. 2 is a comparable bar graph showing levels of bacteria tolerant to heavy metals in the same exploration area as determined by the fast luminometry technique of this invention.

FIGS. 3-11 are a series of concentration contour maps relating to a known subsea oil field MC 486-531 in an offshore area of Louisiana, with:

FIGS. 3-8 showing microbiological survival rate contours of bacteria sampled in MC 486-531 from 1 meter below the seabed for:

FIG. 3—50 ppm Cobalt;
FIG. 4—100 ppm Cobalt;
FIG. 5—10 ppm Ni;
FIG. 6—20 ppm Ni;
FIG. 7—4% pentane;
FIG. 8—4% hexane; and FIGS. 9-11 showing ambient sediment metal concentrations in the same MC 486-531 area;

FIG. 9 showing V contours;
FIG. 10 showing Ni contours;
FIG. 11 showing Zn contours;

FIGS. 12-21 are a series of concentration contour maps relating to an undrilled raw prospect subsea federal lease area MC 665-710 also offshore of Louisiana, with:

FIGS. 12-19 being comparable to FIGS. 3-8 as showing microbiological survival rate contours of bacteria sampled from MC 665-710 from 1 meter below the seabed for:

FIG. 12—50 ppm Cobalt;
FIG. 13—100 ppm Cobalt;
FIG. 14—10 ppm Ni;
FIG. 15—20 ppm Ni;
FIG. 16—20 ppm Zn;
FIG. 17—4% pentane;
FIG. 18—4% hexane; and FIGS. 19-21 showing ambient sediment metal concentrations in the same MC 665-710 area; with FIG. 19 showing V contours;
FIG. 20 showing Ni contours;
FIG. 21 showing Zn contours; and FIG. 12 also showing location of an oil well drilled in CM 709-665 which discovered oil, thus proving the efficacy of the methods of the present invention.

DETAILED DESCRIPTION OF THE BEST MODE OF CARRYING OUT THE INVENTION

Figure 4:
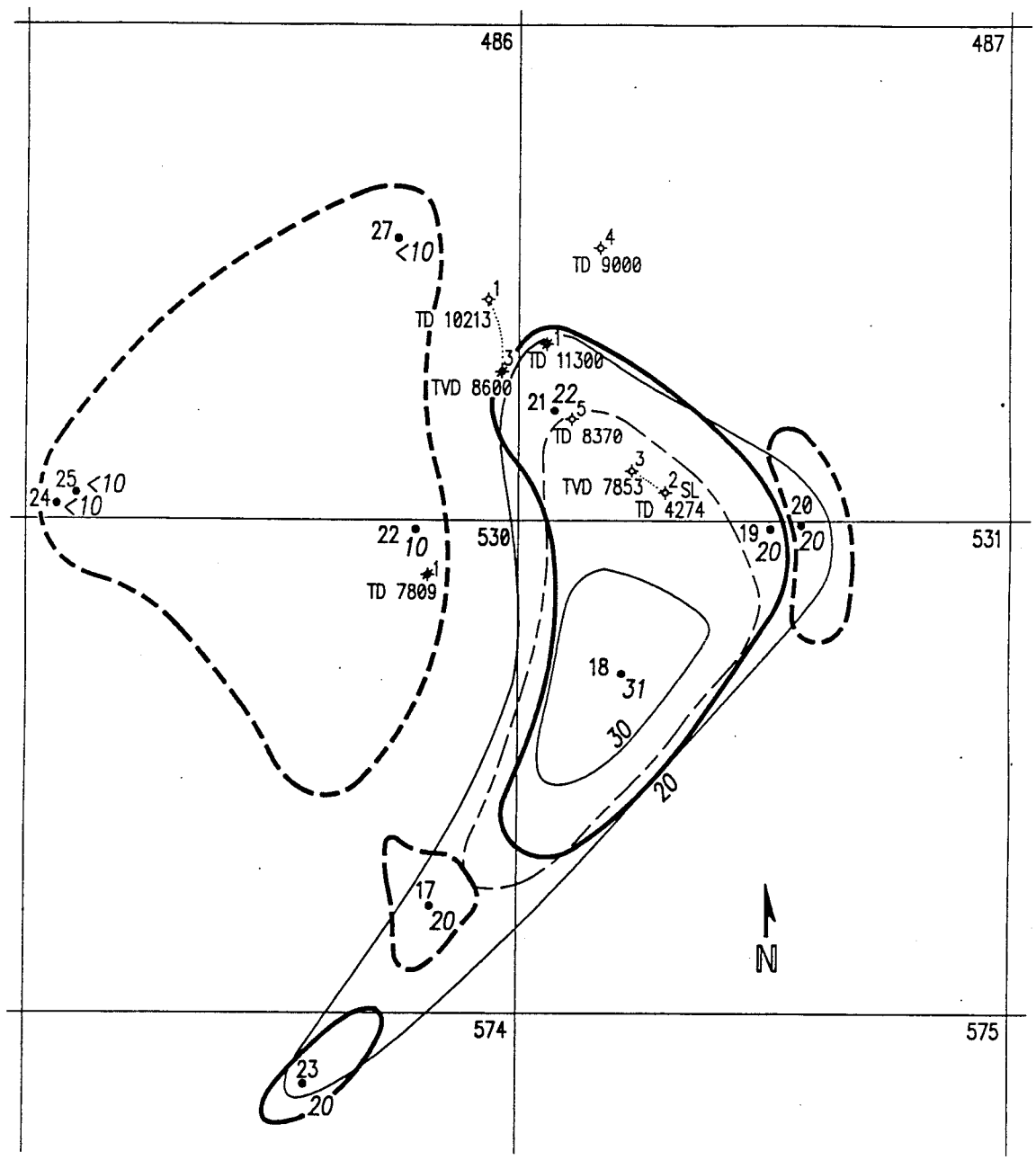

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

DESCRIPTION OF THE STUDY AREAS

A. General Geology—Dry Land

The area where these techniques were tested was the Gold Brick mining district, Gunnison County, Colorado. It lies between longitude 106° 30' and 106° 40'W and latitude 38° 30' and 38° 40'N.

The rocks which outcrop in the area range in age from Precambrian to Holocene. The Precambrian bedrock is largely metasediment; the Paleozoic and Mesozoic rocks are sedimentary and igneous intrusive in origin; and the Tertiary rocks are volcanic and hypabyssal intrusives. Outcrops are rare because the entire area is thinly blanketed by various types of glacial deposits and talus which support dense vegetation.

Structural development of the terrain was complex and is dominated by Laramide folding, normal faulting, and thrusting. The normal faulting dropped Paleozoic carbonates into the Precambrian crystalline rocks where they were preserved and subsequently mineralized (Crawford, 1913; Dings and Robinson, 1957).

B. General Geology—Sub-Sea Area

Federal lease areas in the Mississippi Canyon Area off the Coast of Louisiana were surveyed. First, samples were taken in the blocks MC 486, 487, 530 and 531 to correlate the results of the method of this invention with drilled area having known petroleum accumulations. Then an undrilled raw prospect MC 665, 666, 709 and 710 was surveyed by the method of this invention, an exploration map was developed and a well area targeted. A well was drilled and a hydrocarbon reservoir was discovered.

The 709 salt dome is centered in an intersalt basin bounded by salt ridges and growth faults. Pleistocene Q-2.5 to present deposition within the basin is the result of rapid eustatic sea level changes ($+/-200'$) related to glacial and interglacial stages. High sediment input at the end of the glacial stages resulted in shelf edge deltas and associated turbidite fans on the continental slope in water depths greater than 600'. Turbidite sands were deposited in bathymetric lows between salt highs that resulted from previous loading in the basin. Turbidite fans of Q-1, Q-1.5, and Q-2.5 age within the 709 basin correspond to chaotic, discontinuous seismic facies. These seismic facies can be tied into well control to the north, where they correspond to sand-rich sections in the up-dip portion of the fans.

II. DESCRIPTION OF THE DEPOSITS

A. Dry Land—Ore

Ores of the Gold Brick district are mainly fissure-vein deposits. Significant replacement of both carbonate and crystalline wall rocks has taken place locally although replacement deposits per se are not generally common in this district, the Zn ores of the Carbonate King being the notable exception. Contact metamorphic deposits of Fe ores have also been mined (Crawford and Worcester, 1916). None of the deposits are horizontally continuous; vertical shoots constitute the principal ore body geometry.

Galena is the dominant ore mineral although gold and silver are the elements of economic interest in the district. Chalcopyrite, sphalerite, and molybdenite are present in varying amounts and all of these also host Au and Ag. Surface oxidation is extensive, but almost none has been recorded more than 100 ft (30 m) below the surface (Dings and Robinson, 1957).

The area was selected for our study because the ore deposits and mining wastes provide a strong metal influx to area streams. There is limited human activity and no permanent dwellings, although grazing allotments for cattle are utilized in some parts of the drainage. Finally, the area we examined is confined to one ecozone so we expected to be able to establish background responses for the same species that we were sampling in the mineralized reaches of the stream.

B. Sub-Sea—Petroleum Deposits

These were typical accumulations of the Mississippi Canyon region. The Mississippi Canyon Block 709 play is a downthrown fault trap located on an anticlinal nose dipping northward from the 709 salt dome. The trapping down-to-the-northwest growth fault system parallels the salt face at depth (Q-2.5), where the salt elongates into a ridge. This fault system separates the Q1.5 through Q-2 downthrown play from the Q-1 salt piercement of the southern portion of the dome and a related radial fault pattern. The downthrown play is relatively unfaulted compared to the Q-1 piercement structure. Initial formation of the downthrown play is thought to have occurred during Q-2.5 time when the fault system developed in response to sediment loading in the basin directly west of the Q-2.5 salt ridge. The downthrown trap persisted through Q-1.5 time with continued loading to the west and growth on the fault system. Growth and structure diminished after Q-1.5 time as sediment loading shifted to the east of the salt dome.

III. METHOD

A. Sample Types

Aquatic systems offer three types of possible samples for microbiological analysis; grab samples, which represent the water column; sediment samples, which represent stream bottom or sea bottom populations; and samples of sessile populations which are present in a polysaccharide matrix on surfaces within streams.

Of these three types, grab samples are by far the easiest to collect on dry land prospecting and are he most representative of the drainage area as a whole. This is because they contain not only the native aquatic populations characteristic of the stream environment, but also organisms which may have been carried into the stream by snow melt, run-off or animals.

Sediment samples represent populations of longer residence time in a particular area, but are less representative of the surrounding environment in the case of dry land exploration but can be used in the methods of this invention. In addition, the sediment may contain clays or other particulate materials which bind metals and therefore decrease the toxicity (Babich and Stotzky, .1980; Gadd and Griffiths, 1978). For subsea exploration, we preferred and used surface sediment samples collected offshore with conventional piston-coring devices, taking a split about 1 meter down from the seafloor surface. This assured obtaining anaerobic bacteria whose energy sources could include methane.

Samples of the sessile populations also represent long residence time in land stream environments, but these are more difficult to obtain and to quantify. Furthermore, the polysaccharide matrix in which they are found also tends to bind metals, thus reducing the exposure of the bacteria to the toxic metal species present in the water (Costerton and Irvin, 1981).

We have found grab samples best for evaluating land stream systems. The bacteria from these samples are predominantly aerobic. These do contain the fewest organisms, however, and the distribution may be uneven, which requires that somewhat more care be taken during sampling and in the execution of experimental procedures (El-Shaarawi et al., 1981; Jones and Simon, 1980; Klein and Wu, 1974; Kosinski et al., 1979).

B. Microbiological Sensitivity Assays

While culture methods can be utilized to demonstrate the presence of metal resistant bacteria in a land or sub-sea environment, these methods require 5–7 days of incubation and necessitate facilities for the preparation of media, incubation of cultures, and subsequent disposal of the spent culture material. Furthermore, it is well known that culture methods enumerate only a small fraction of the bacterial population present in an environment, those whose physiological requirements are met by the composition of a particular medium (Albright et al., 1972; Fry and Zia, 1982; Fuhrman and Azam, 1982; Jonas et al., 1984; Karl, 1980). Another group of methods for detecting the total microbial population in a system, rather than only those organisms which can be grown on a specific culture medium, involves the use of radioactive labels. Many of the older methods involve use of an organic molecule labelled with carbon-14 (Albright et al., 1972; Goulder, 1980; Jonas et al., 1984). These methods can be used to detect both incorporation of the isotope into the cells and the degradation of the carbon-containing molecule for energy, which produces radio labelled carbon dioxide. The chief problem with carbon-14 labelling is that not all microorganisms use the same organic molecules as a source of carbon and energy (Jonas et al., 1984). Thus, these methods, like culture methods, only detect part of the population, although the numbers or organisms will be higher using isotopes if the carbon source is carefully chosen for the environment being studied. In order to assess environmental populations more effectively. This invention employs luminometry and/or tritiated thymidine isotopy to assay the entire bacterial population.

B.1. Luminometry

The most rapid and preferred assay for field testing is luminometry, the use of the "firefly light" or bioluminescence enzyme reaction and an instrument containing a photocell to measure the amount of light generated:

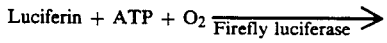

$$\text{Luciferin} + \text{ATP} + \text{O}_2 \xrightarrow{\text{Firefly luciferase}}$$

$$\text{Light} + \text{AMP} + \text{PP}_i + \text{CO}_2 + \text{Decarboxyluciferin}.$$

Because the reaction is directly dependent on ATP, a molecule which is present in all cells, the amount of light generated is a measure or how much ATP is present and hence the number of cells present in a sample (Karl, 1980).

Early attempts to use luminometry for determining cell numbers in environment samples were often frustrated by problems with ineffective methods of removing ATP from the cells present in a sample and with binding of ATP to glassware. Extreme fluctuations in the data obtained were common, and statistical reliability was often highly questionable. These problems have now been largely corrected by the use of plastic tubes and the development of specialized reagents for extraction of ATP from various types of cells. Packaged reagents for the enzyme system with optimum concentrations of reactants are also being produced by the companies which market luminometers.

The sample volume required for luminometry is usually quite small, less than that required for culture methods because all of the organisms present in the sample can be detected. In the oligotrophic land-based stream waters in the land study area described tested sample volumes of 100 ul per assay were sufficient. For subsea sediment sampling sample volumes on the order of 120g of sediment suspended in 250 ml distilled water is sufficient. The sediment is thoroughly suspended in water and centrifuged. The supernatant is used in the tolerance testing. If samples are encountered in which the levels of bacteria are below detection limits in a 100 ul sample, the bacteria can be concentrated by membrane filtration (Karl, 1980).

The concentrations or metals and hydrocarbons required to determine resistance in oligotrophic streams or seabeds are set forth in Table 1. As used herein "u" in ug, ul, or um means "micro".

TABLE 1

Metal Concentrations to Determine Tolerance

| Metal (or ion)/Hydrocarbon | Concentration (ug/ml)* (Volume Percent)** |
|---|---|
| Land Exploration | |
| Arsenate (as sodium arsenate) | 2000, 4000 |
| Cadmium (as cadmium chloride) | 10, 25, 50, 100 |
| Copper (as copper sulfate) | 50, 100, 150, 200 |
| Lead (as lead acetate or nitrate) | 500, 750, 1000 |
| Mercury (as mercuric chloride) | 5, 10 |
| Tellurium (as potassium tellurite) | 150, 250, 500 |
| Zinc (as zinc chloride) | 2000, 4000 |
| Subsea Exploration | |
| Cobalt | 50, 100 |
| Nickel | 10, 20 |
| Zinc | 20 |
| Pentane | $10^a$ |
| Hexane | $10^a$ |

*Concentrations of metal ion.
**Concentration for hydrocarbons
$a$.1 ml in a 1 ml aliquot = 10 vol %; range is .001–25% by volume for hydrocarbons generally A range of concentrations should be utilized for each metal and hydrocarbon in luminometry or isotopy, as well as in culture assays.

The individual metal compounds listed in Table 1 are predissolved in distilled water and are then added in appropriate amounts to 1 ml aliquots and incubated for 1–3 hours, preferably 2 hours, while being continually shaken on a shaker table or wrist action shaker. The temperature should be maintained constant in all tests to be compared within a range of from 20–25 degrees C, unless the normal microbial habitat is cold, say above 300 meters or seafloor. In such case the temperature should be close to habitat temperature.

For hydrocarbon tolerance tests, 0.1 ml of hexane, pentane or other hydrocarbon is added to a 1 ml and axially spun to from a vortex. The incubation is from minutes, preferably 3–5 minutes. Lower concentrations of hydrocarbons, or shorter incubation periods may be employed. Thus a range of from 0.01% to 25% by volume may be employed. The temperatures should be below about 20 degrees C., and as close to habitat temperature as feasible.

Regarding sample pH, the aquatic samples from the Western Slope exploration area described herein was in the neutral to slightly alkaline range of pH 7–7.8 and needed no pH adjustment. Likewise, since the seabed seabed are suspended in distilled water they were in the neutral range. Where a sample is acidic, the pH can be adjusted with dilute KOH. Inorganic non-phosphate buffers, such as sodium bicarbonate can be used to adjust pH if need be, but most systems will be in or close to neutral pH range. Mine drainage area samples are expected to be acidic and require pH adjustment.

The actual concentrations of heavy metals or hydrocarbon toxics to be evaluated will depend on the specific system being studied, because certain ions and organic compounds as well as the pH of the system will affect the toxicity of metals (Babich and Stotzky, 1980; Gadd and Griffiths, 1978; Jardim and Pearson, 1985; Laegreid et al., 1983). The time required to inhibit sensitive organisms in an experimental system is 2 hrs (Babich and Stotzky, 1980; Bell et al., 1980; Schneck, unpublished data).

Stock solutions with suitable concentrations of metal ions and/or hydrocarbon (pentane, hexane) toxics are added to aliquots of the sample and incubation in the of the metals can be carried out for several samples at one time. After 2 hrs., .0.1 ml aliquots from the metal incubation mixtures as well as controls without metal additions are assayed for the quantity of ATP present by luminometry. The number of cells present per milliliter of the original samples can then be calculated on the basis of quantity of ATP per cell. In these experiments, 1 fg (femtogram) ATP per cell was used as the basis for calculations.

Because heavy metals can inhibit enzyme catalyzed reactions due to effects on the structure of the enzyme, some metals may cause a loss of activity at the concentrations required for determining resistance. This can be detected by an internal standard of ATP which should be used in all procedures (Karl, 1980). Of the metal ions tested in this survey (arsenate, Cd, Cu, Pb, Hg, Ag, tellurite, Zn, Co, Ni and V), only Cu inhibited the luminescence system: the presence ug/ml Cu completely halted the reaction. If Cu is the metal in question, or if it is being used as a pathfinder, the bacterial population can be removed from the Cu incubation mixture by membrane filtration. The cells can then be resuspended in distilled water for the assay.

Another potential problem which can occur with luminescence systems is the presence of the enzyme alkaline phosphatase in phosphate limited environments (Jones, 1972; Karl, 1980; Reichardt et al., 1967). Alkaline phosphatase rapidly degrades ATP and, if present, can lead to incorrect measurements of the ATP present in a sample (Karl, 1980; Karl and Craven, 1980). Methods are available to account for the effects of alkaline phosphatase if it is present (Karl and Craven, op. cit.), but no elevated levels of phosphatase were encountered in these tested environments.

It is necessary to process water samples as quickly as possible in order to prevent changes in the population (Karl, 1980). Stream samples are collected in small Whirl Pak bags and maintained at approximately the same temperatures as that of the sampling location for transport to the laboratory or field camp by use of insulated containers. Sediments from piston cores are suspended in vials or bottles on deck immediately after recovery. Luminometry can be done in field camp or on board exploration/survey ship where a generator is available. Depending upon the number of metals being used in a particular exploration program, 4–8 complete (including all metal concentrations and controls) can be processed per hour.

B.2. Tritiated Thymidene Isotopy

The methods of this invention are based in part on the observations that one way to detect a larger fraction, perhaps most, of the organisms present in an environment is to use a labelled compound which virtually all organisms utilize. Thymidine, which is required for the synthesis of DNA, is an example of this type of molecule. Accordingly, this invention employs tritiated thymidine as a methodology to measure the effects of toxicsubstances on aquatic ecosystems (Fuhrman and Azam, 1982; Jonas et al., 1984). This method is relatively specific for bacteria, with minimal interference from other types of cells, and appears to label all actively growing bacteria (Fuhrman and Azam, op. cit.). While it is not a preferred field method because it requires the use of a liquid scintillation counter, this method can be utilized if laboratory facilities are available, for example, on board exploration/survey/research ship. Thus, use of tritiated thymidine does represent an additional method for assessing the "total" bacterial population, and it can also be used as a check on the effectiveness of the luminescence system. It can also be utilized in samples having compounds or elements which adversely affect the enzyme used in luminometry.

To use the tritiated thymidine method, 10 ml aliquots of the land based water sample or the suspended sealed sediment supernatant are place in flasks with the addition of 0.5-1 uC of thymidine and the desired metal or hydrocarbon. A sample filtered through a 0.2 um filter to remove cells is used as a blank. After incubation (1-2 hours for metals, 3-5 minutes for hydrocarbons), trichloroacetic acid is added to the flasks, the flasks are chilled in an ice bath, and the mixture is filtered through a 0.2 um membrane filter to trap labelled particulate material (Jonas et al., 1984). The filters are then placed in scintillation vials containing a suitable cocktail (Fisher Scintiverse was used in these experiments) and counted in a liquid scintillation counter.

Calculations obtained from use of tritiated thymidine or other isotope incorporation methods yield results indicating "significant" or "not significant" differences between samples, rather than numbers of bacteria per ml, unless a curve to relate disintegrations per minute (d/min) of the isotope to number of cells is determined. For exploration programs, differences between sites provide sufficient information; the actual numbers of cells are not needed.

IV. RESULTS AND DISCUSSION

A. Land Assays—Heavy Metal/Ore Exploration

Data previously presented by Michaels and Riese (1986) using the culture assay method demonstrated that streams of the Gunnison watershed have a bacterial population with significantly higher levels of metal resistance than has been generally reported (Haefeli et al., 1984; Houba and Remacle, 1980; Sjogren and Port, 1981; Timoney et al., 1978; Varma et al., 1976). These increased levels of resistance were interpreted as due to the presence of weathering mineral deposits in the drainages of the Gunnison basin. When specific streams originating above areas of mineralization were examined, elevated levels of metal resistant bacteria were found below the mineral deposits.

These results were confirmed in this study of Gold Creek in the Gold Brick district The results for three sites along Gold Creek as determined by culture, luminometry and isotope incorporation using tritiated thymidine are presented in Table 2 and FIG. 1 and FIG. 2. Site GC-1 is above all recorded mines and mineral deposits; GC-5 and GC-7 are approximately ½ mile (0.8 km) and 1 mile (1.6 km) respectively below the known mineralization.

TABLE 2

Comparison of Gold Creek sites

| Site | Culture method (CFU/ml)* | Luminometer (cells/ml) | Thymidine uptake (d/min) |
|---|---|---|---|
| GC-1 | Control 462 | Control $2.95 \times 10^5$ | Control 624.85 |
|  | Cd 50 4 (1) | Cd 50 $3.27 \times 10^4$(11) | Cd 318.6 |
|  | Cu 200 16 (5) | Cd 100 $4.32 \times 10^4$(15) | $P = 0.001$ |
|  | Hg 5 0 (—) | Hg 5 $1.25 \times 10^5$(42) | Hg 329.25 |
|  | Te 250 1 (1) | Hg 10 $7.42 \times 10^3$(2) | $P = 0.001$ |
|  |  | Te 250 $2.45 \times 10^3$(1) |  |
|  |  | Te 500 240(<1) |  |
| GC-5 | Control 600 | Control $2.50 \times 10^5$ | Control 408.9 |
|  | Cd 50 120 (20) | Cd 50 $2.25 \times 10^5$(90) | Cd 231.75 |
|  | Cu 200 64 (11) | Hg 5 $1.75 \times 10^5$(68) | $P = 0.001$ |
|  | Hg 5 0 (—) | Te 250 $1.93 \times 10^5$(77) | Hg 239.0 |
|  | Te 250 6 (1) |  | $P = 0.01$ |
|  |  | Control $1.81 \times 10^5$ |  |
|  |  | Cd 50 $2.18 \times 10^5$(>100) |  |
|  |  | Cd 100 $3.14 \times 10^5$(>100) |  |
|  |  | Hg 5 $8.97 \times 10^4$(50) |  |
|  |  | Hg 10 $8.00 \times 10^4$(44) |  |
|  |  | Te 500 $3.17 \times 10^4$(17) |  |
|  |  | Te 500 $1.76 \times 10^4$(10) |  |
| GC-7 | Control 1530 | Not done | Control 399.85 |
|  | Cd 50 160 (11) |  | Cd 276.40 |
|  | Hg 5 81 (5) |  | Not significant |
|  | Te 250 no valid data |  | Hg 394.00 not significant |

*CFU-colony forming units/ml of original sample.
Cells/ml calculated on the basis of 1 fg ATP/cell.
d/min-disintegrations/min.
Numbers in parentheses refer to percent of control.

By all three methods, site GC-1 can be shown to have a bacterial population which is highly sensitive to the toxic effects of the metals tested. These data also indicate the differences in bacterial numbers which can be detected with luminometry vs. the cultural method. Using the best medium available, culture can only detect an average of 462 colony forming units of bacteria per milliliter of the original sample, while luminometry indicates $2.95 \times 10^5$ bacteria per ml. The differences between culture and luminometry usually become more pronounced in highly oligotrophic streams, as is clearly illustrated here.

It is also evident that a higher proportion of the total bacteria, as detected by luminometry, is resistant to the effects of metals. This is true of both the control site, GC-1, and of the sites affected by mineralization. As noted above, isotope incorporation data does not indicate actual numbers of bacteria, but rather statistical significance of differences between sites. At GC-1, both Cd and Hg significantly depress the population. At GC-5, the effects produced by Cd have a higher significance level than that of Hg, while at GC-7 neither Cd nor Hg has a significant effect on the population.

Samples obtained from a mine adit along Gold Creek and from within an active mine in the drainage area showed very low levels of cultivable bacteria (less than 10 CFU/ml). These sites could not be tested by luminometry or isotope incorporation because of extremely limited access. However, culture data suggest that very low numbers of bacteria may be present in the water within, or draining from, a mine. Assuming culture assay is correct, then mine effluent could be so concentrated in toxics as to lower the numbers of bacteria in the waters downstream. The actual numbers of organisms may be decreased by dilution with water containing fewer bacteria or by toxicity of the effluent due to metal content and/or acidity. The thymidine uptake data from Gold Creek, shown in Table 2, suggest that metal toxicity may be the cause, because higher levels of Cd and Hg resistant bacteria were observed further from the mines (site GC-7). In an exploration program involving areas which had not previously been mined, this problem would not be encountered. However, where an area had been mined earlier for another mineral, the possible effects of mine effluent should be considered.

As was observed in the culture technique study of Michaels and Riese (1986), early season data when soil bacteria are being brought into the stream by snow melt and run-off would appear to give the best results. A complete field season profile was not available for Gold Creek due to inaccessibility in the part of the season. Late season samples, however, did show a decrease in differences between control and mineralized location. This is probably due to decreased run-off as well as seasonal in the aquatic bacterial populations (Bell et al., 1980; Costerton and Irvin, 1981; Goulder, 1980; Haack and McFeters, 1982). Late season samples also showed a decrease in average bacterial size as indicated by difficulties in obtaining a cell-free control by use of 0.2 um membrane filters. If late season sampling is required, use of a 0.1 um filter is recommended. Decrease in average, cell size of the population could affect the amount of ATP/cell which should be used for calculation of bacterial numbers, but site-to-site comparisons within the same drainage would still be valid if the same value were used for all sites and samples.

Interpretation of metal effects on bacterial populations must take several environmental factors into account if the data are to provide a valid basis for exploration. The presence of certain divalent cations, most notably ca and Mg, may markedly affect the toxicity of metals to bacteria (Babich and Stotzky, 1980; Gadd and Griffiths, 1978). Examination of geological information for the area in question should indicate whether elevated levels of these ions are likely to be present in the aquatic or subsea systems. The effects of pH must also be considered: an acidic pH will generally increase the toxicity of metals, while alkaline conditions usually decrease toxicity (Babich and Stotzky, 1980; Gadd and Griffiths, 1978). Neither the presence of divalent cations nor pH effects preclude the use of bacterial resistance as an exploration tool. It may be necessary, however, to adjust (increase) the metal concentrations being utilized in sensitivity assays in order to obtain accurate results. For this reason Table 1 shows a range of concentration, the higher value(s) being used in cases of elevated Ca, Mg or clay presence (see below).

Clay minerals and organic materials may also have a significant effect on metal toxicity. These effects are generally due to the binding of metal ions to the clays or organic molecules, thus reducing the availability of the metals in the system (Babich and Stotzky), 1980; Gadd and Griffiths, 1978; Laegreid et al., 1983). In oligotrophic mountain streams, such as the one used in this study, neither clays nor organic materials presented a problem. If the exploration area had eutrophic streams or high levels of clay in the soils or seabeds, again an adjustment (increase) of the metal concentrations would probably be required to obtain the most accurate data.

The various methods used for determining metal resistance in bacteria are compared on the basis of cost, time frame, number of samples per day, and field utility in Table 3. All three methods are roughly comparable in terms of cost per sample, although luminometry certainly offers the best turn-around in a field-usable system.

TABLE 3

| | Comparison of methods | | | |
|---|---|---|---|---|
| Method | Sites/day (including sample collection) | Field usable | Cost/sample (S) | Time to obtain results (days) |
| Culture | 10–20* | Yes | 7 | 5 |
| Luminometer | 10–20* | Yes (requires generator) | 8–9 | 1 |
| Isotope | 10 | No (Land); Yes (Sea) | 10 | 2 |

*Number of sites which can be processed depends upon difficulty of sample collection.
Cost figure based on three metals per site plus controls.

A more important comparison, and one which cannot be made with this table, is with the costs and turn-around of data customary to inorganic analysis of stream sediments or waters. While the analytical cost per sample may be similar if equal numbers of elements are considered, the return of data using the microbiological samples is an order of magnitude faster. This can be especially important at the reconnaissance stage of exploration because follow-up sampling or mapping need not be delayed until the next field season, as may be the case in areas with short field seasons. It can instead be done the next day, if appropriate.

As is the case with any geochemical exploration program, several metals should be tested for concurrently. Additionally, triplicate samples and at least three concentrations of each metal should be used. This will enhance the statistical reliability of the data and facilitate interpretation.

B. Subsea Assays—Petroleum Exploration

Figure 5:
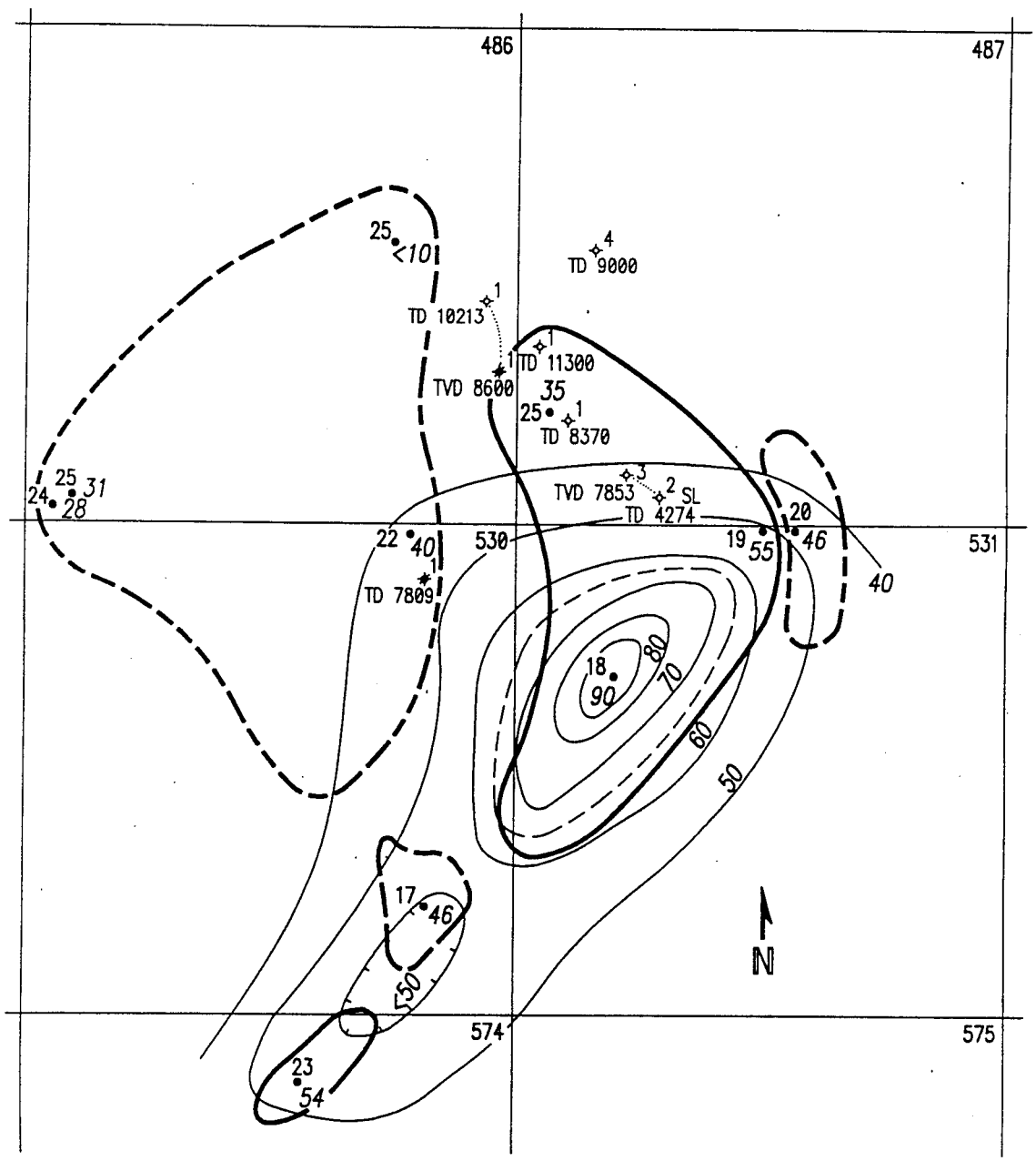
Figure 6:
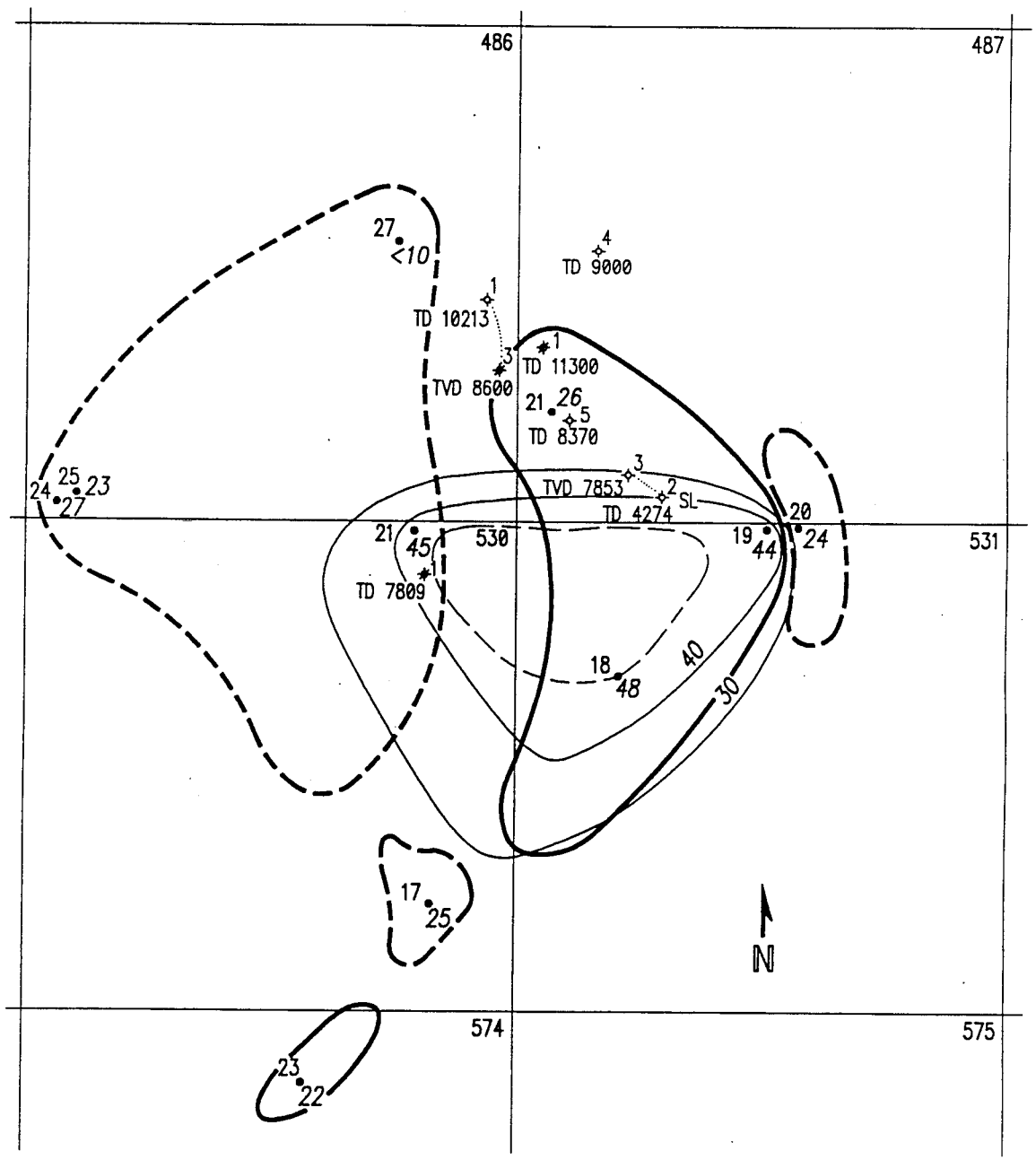
Figure 7:
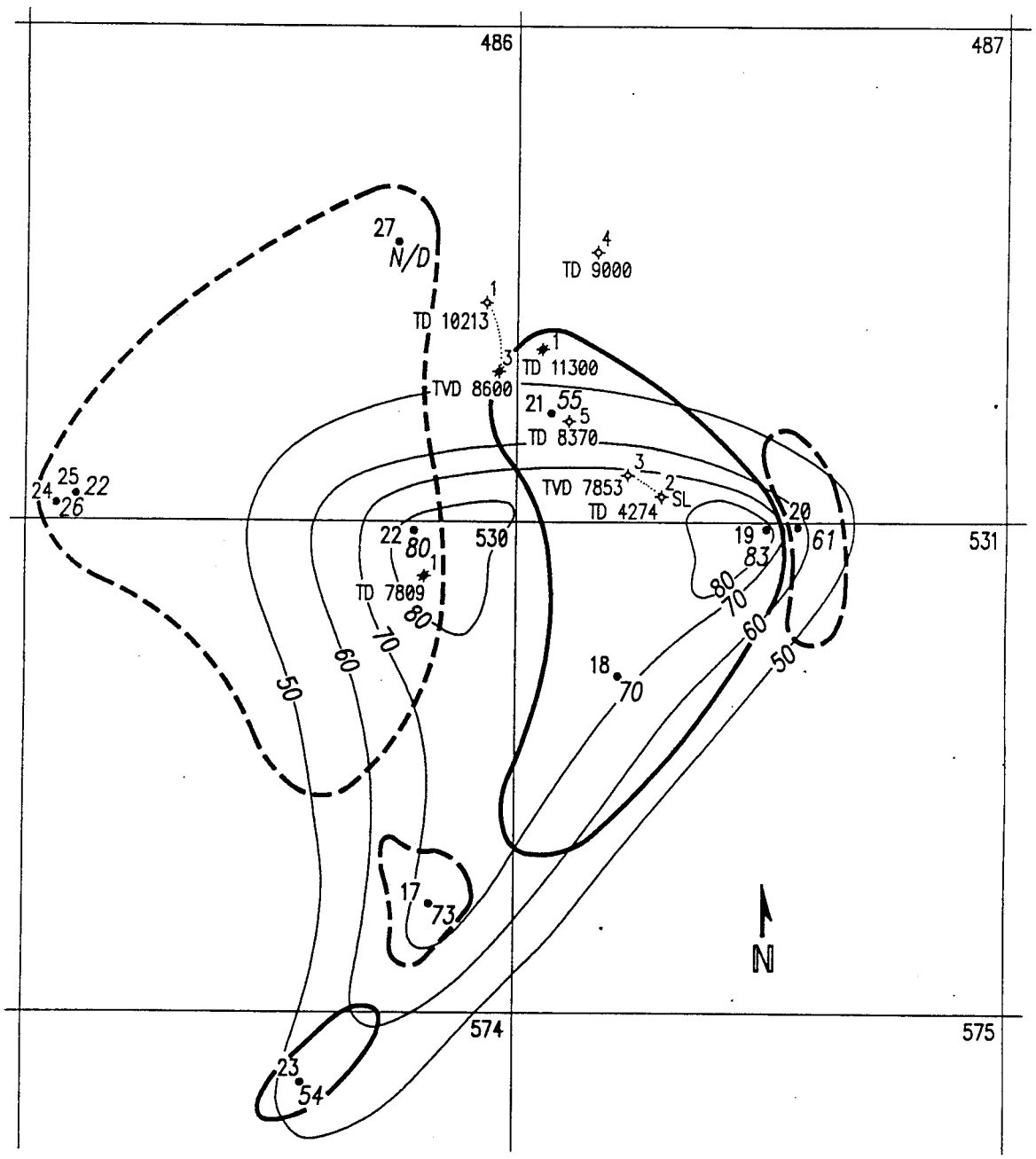
Figure 8:
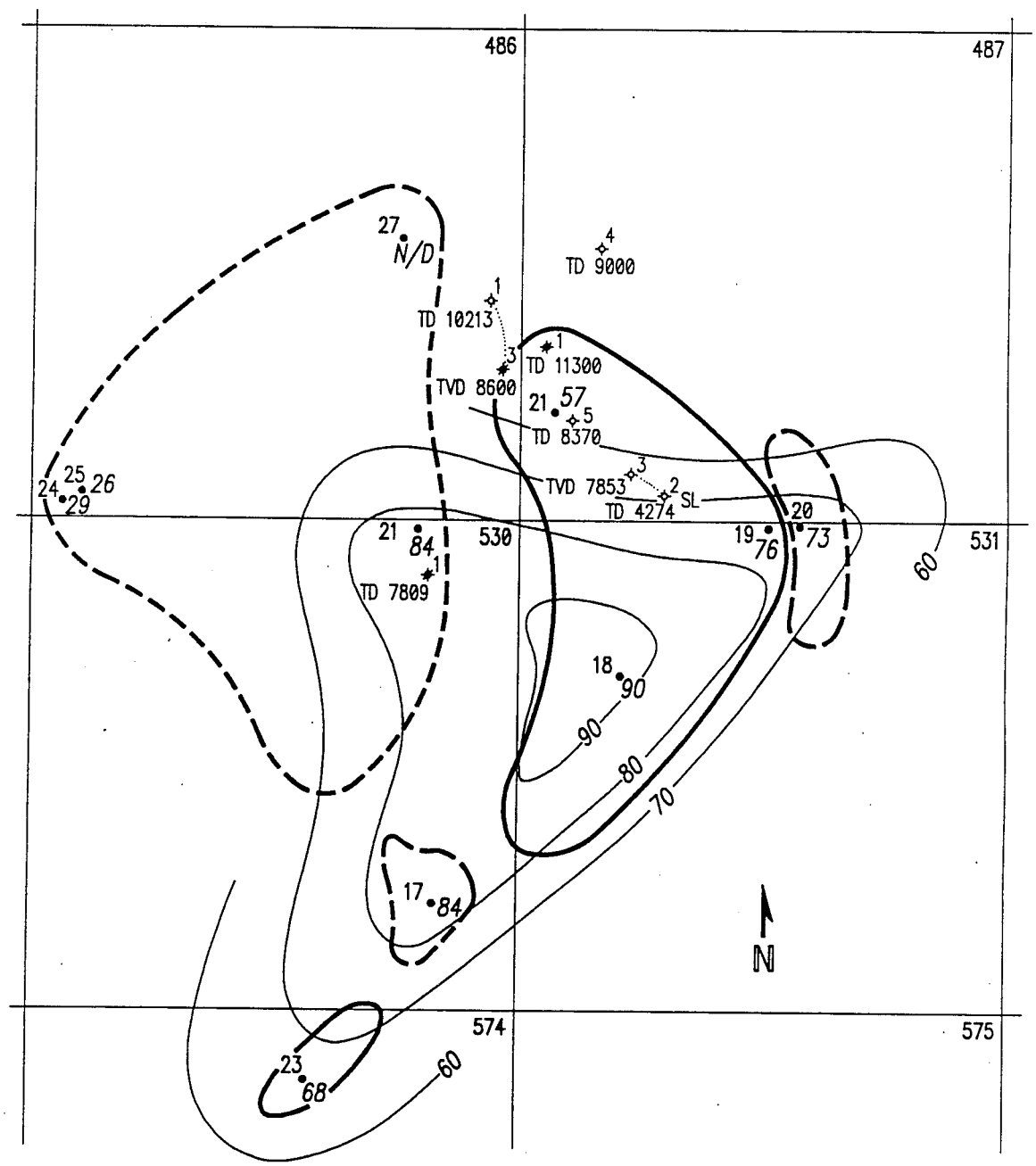
Figure 9:
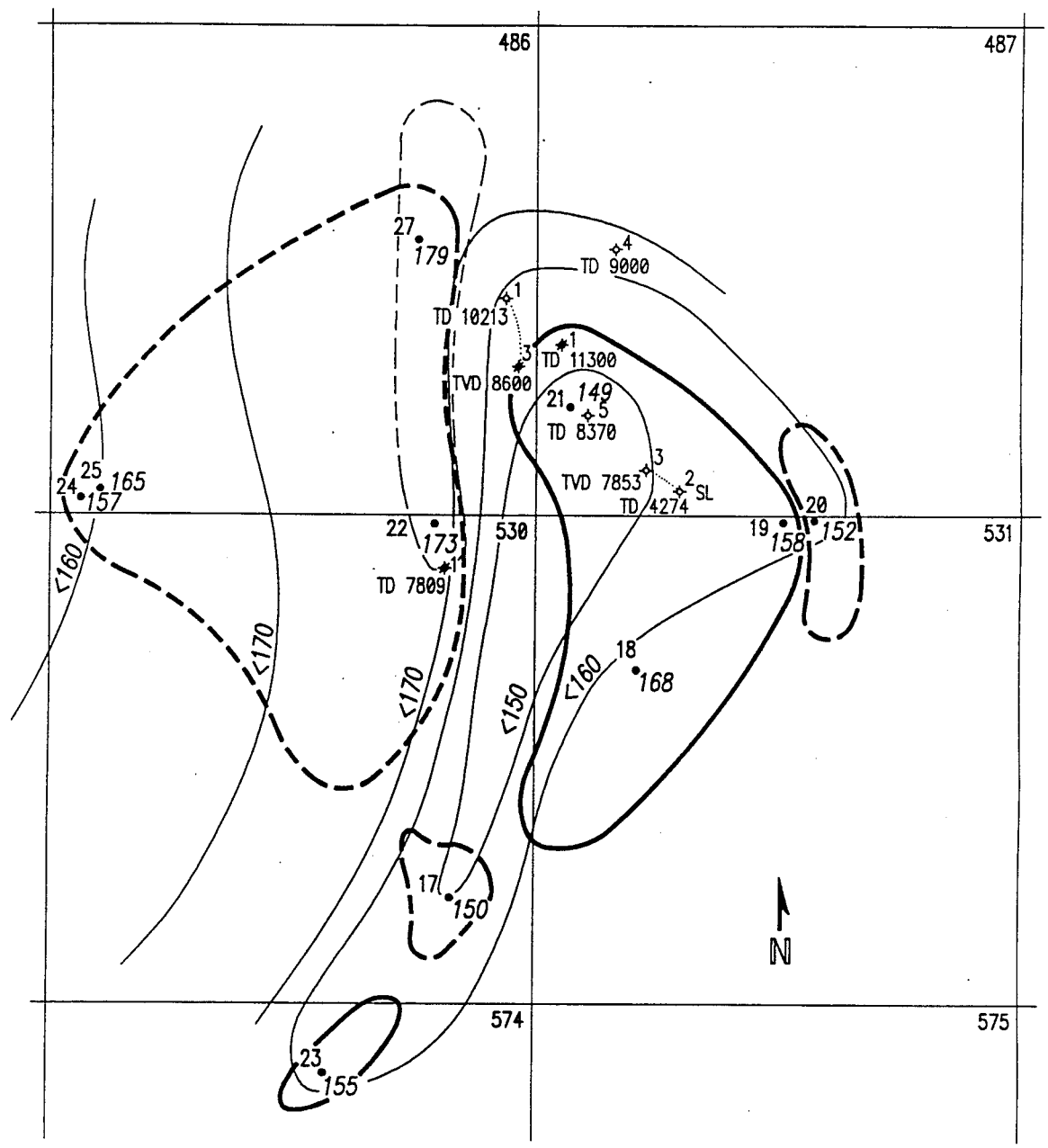
Figure 10:
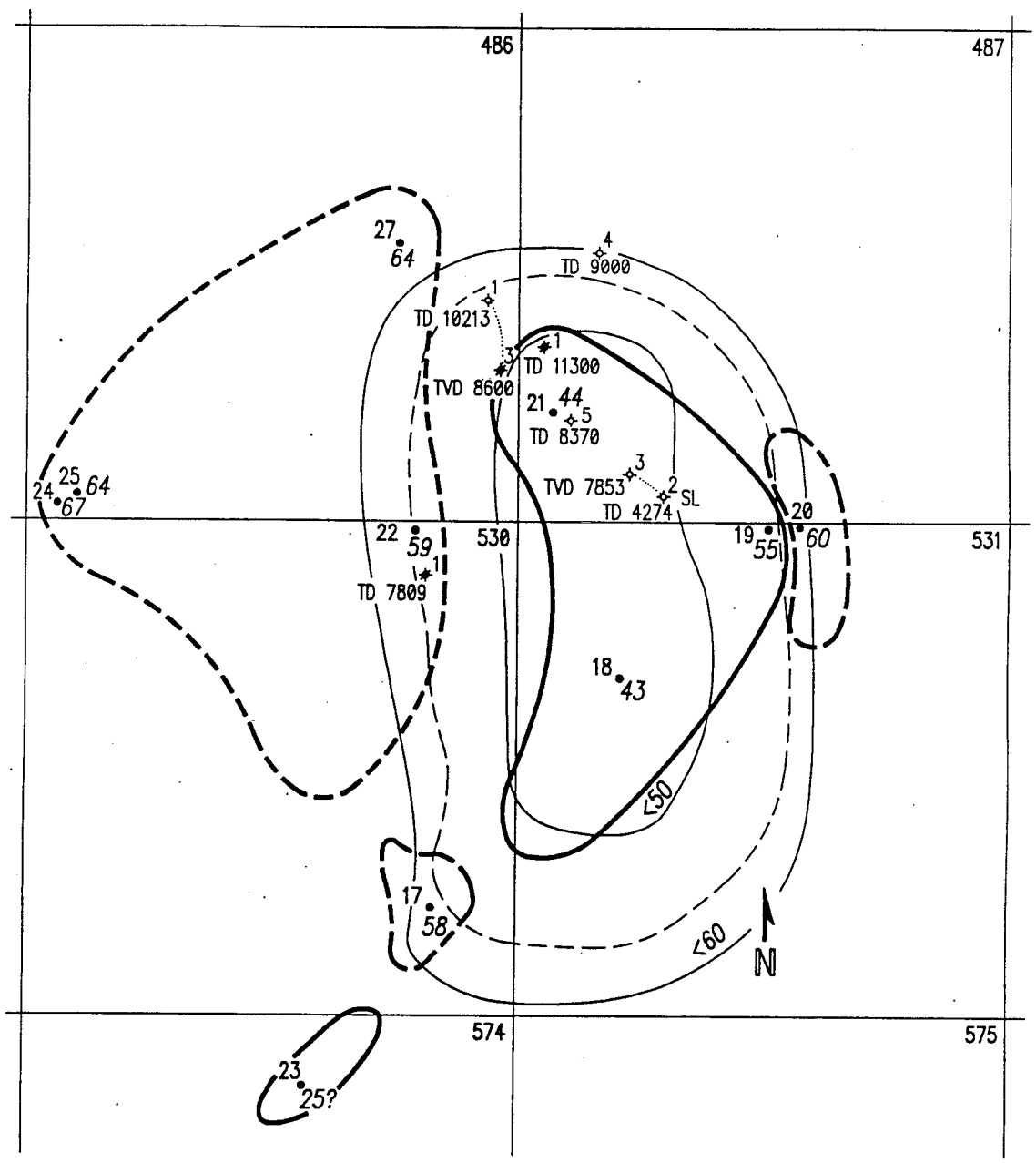
Figure 11:
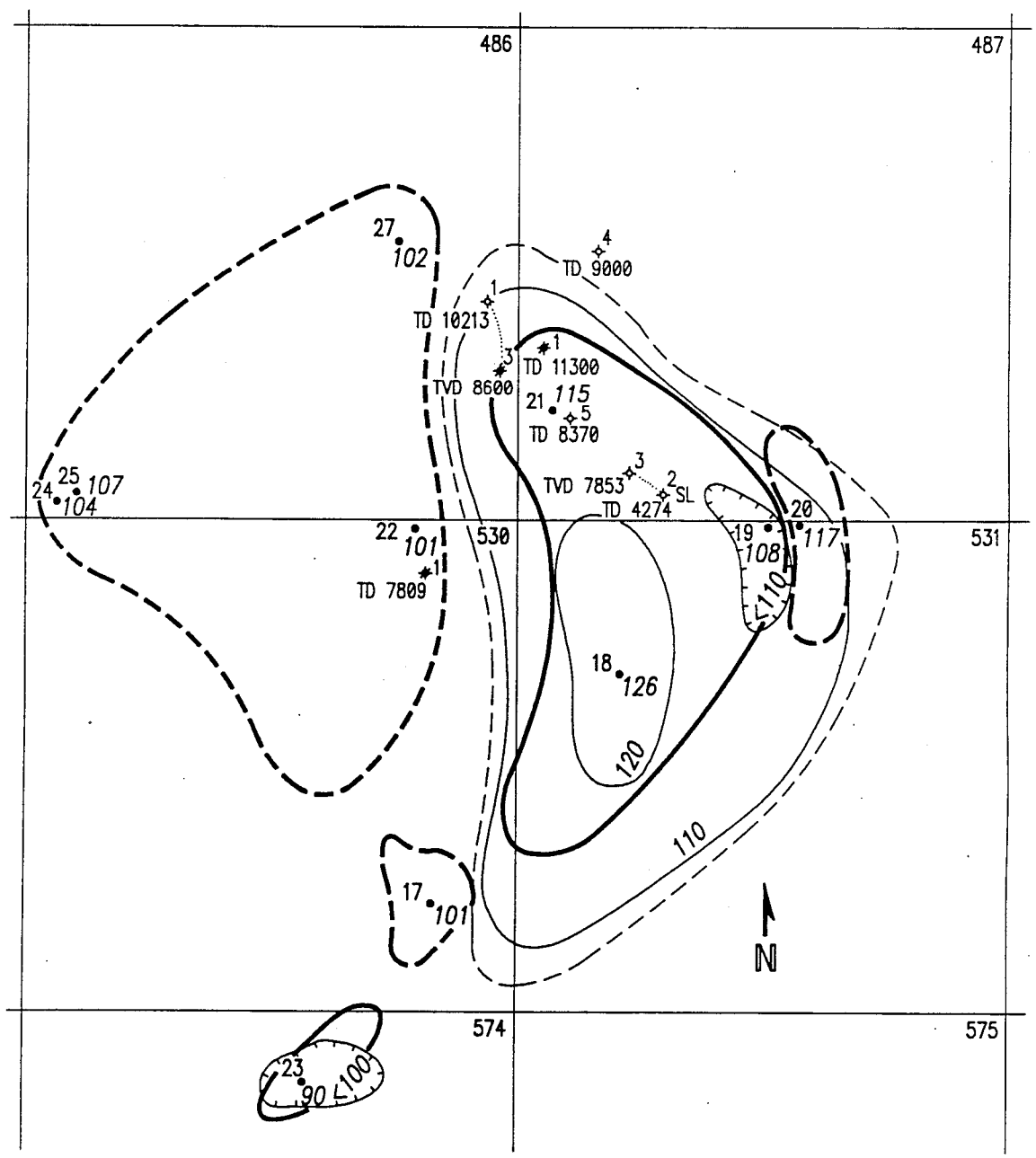
Figure 12:
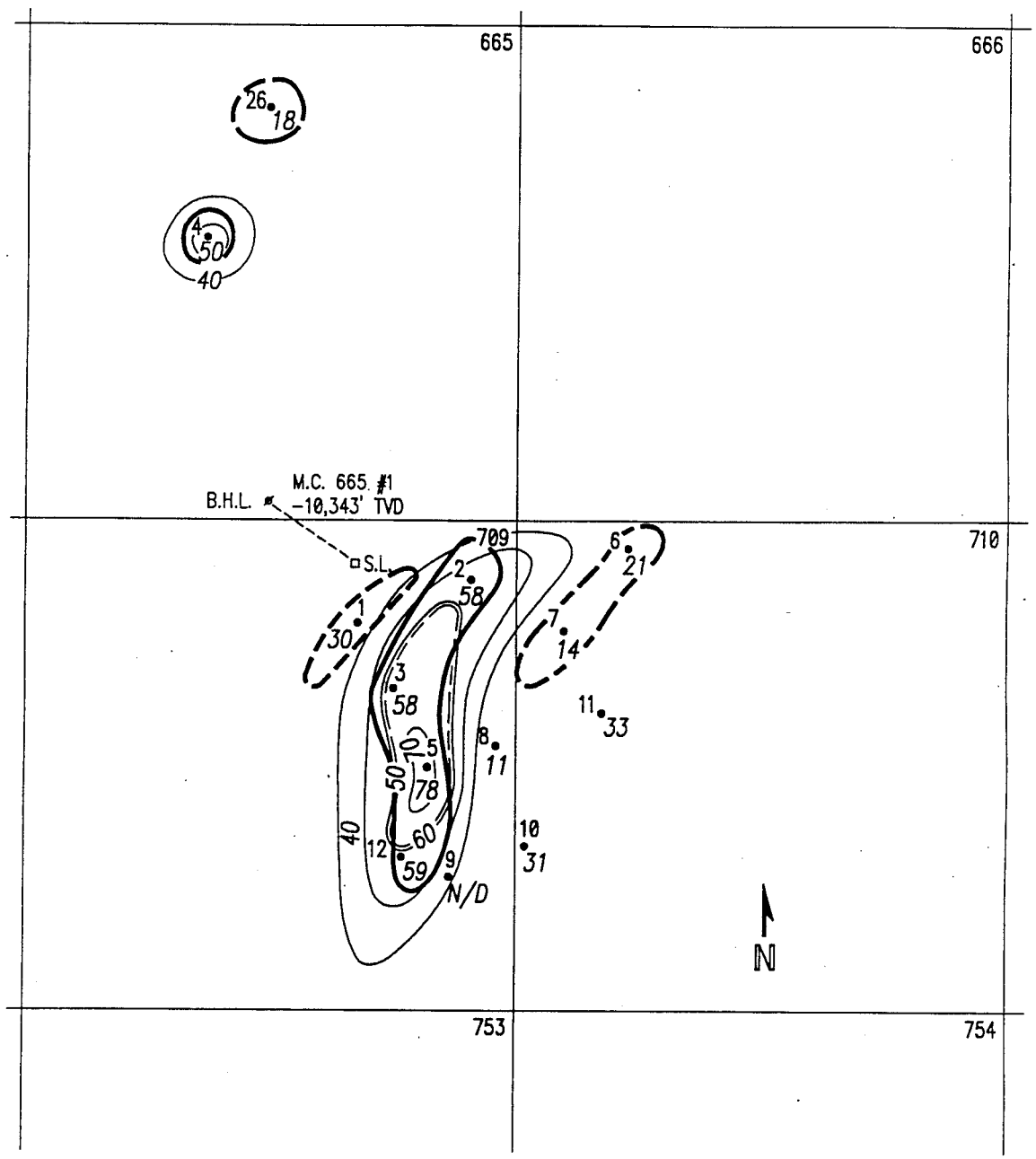
Figure 13:
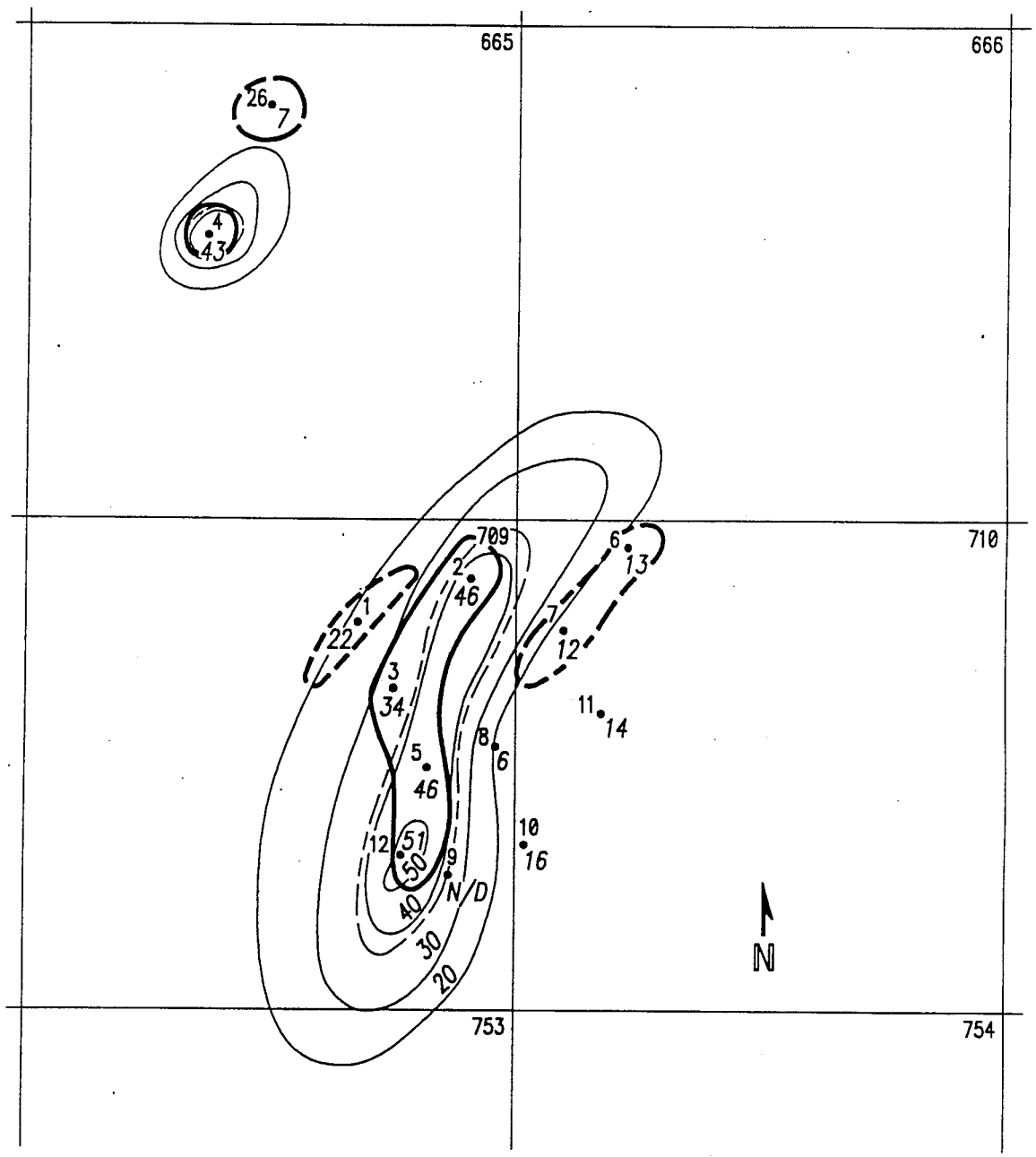
Figure 14:
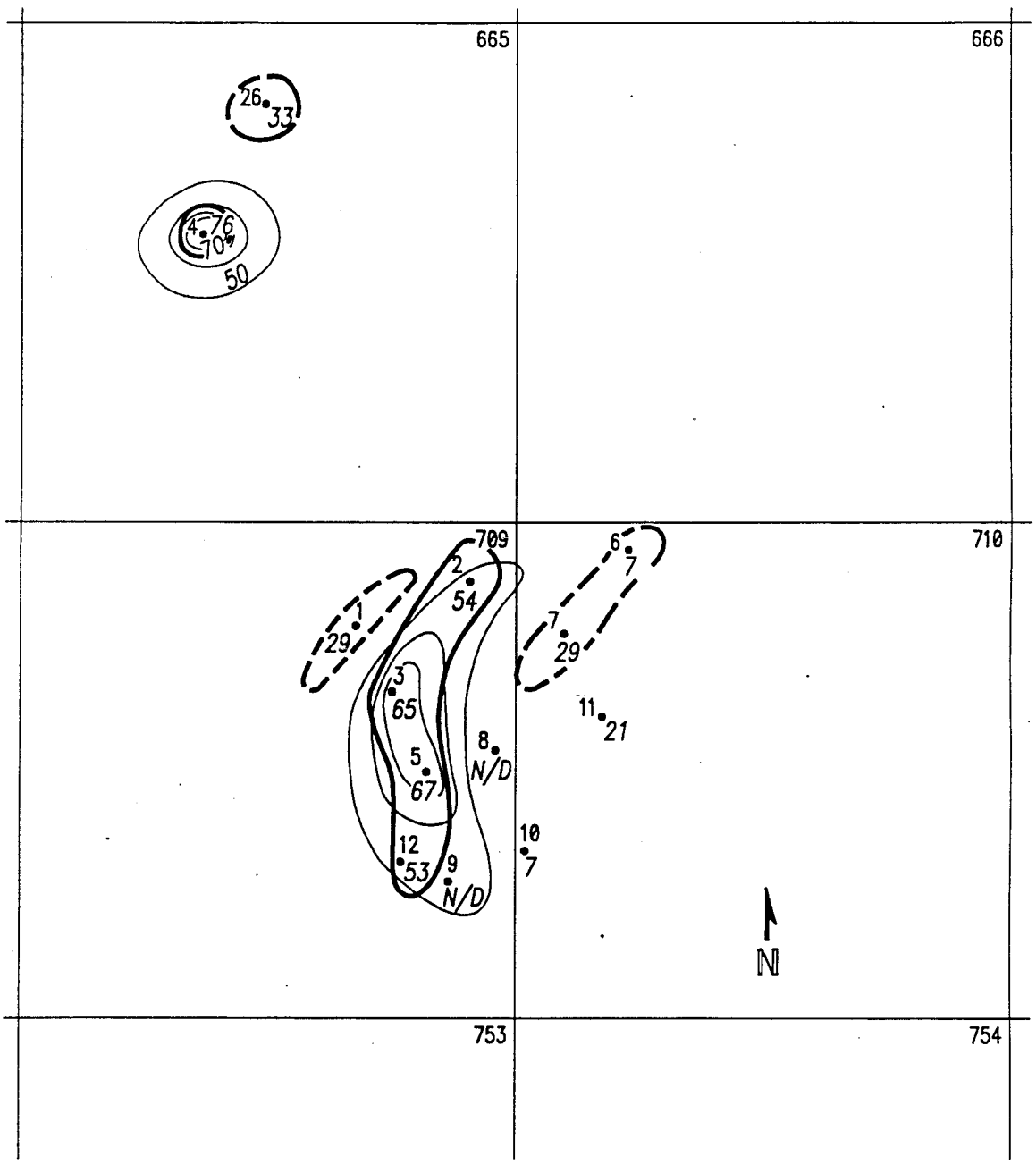
Figure 15:
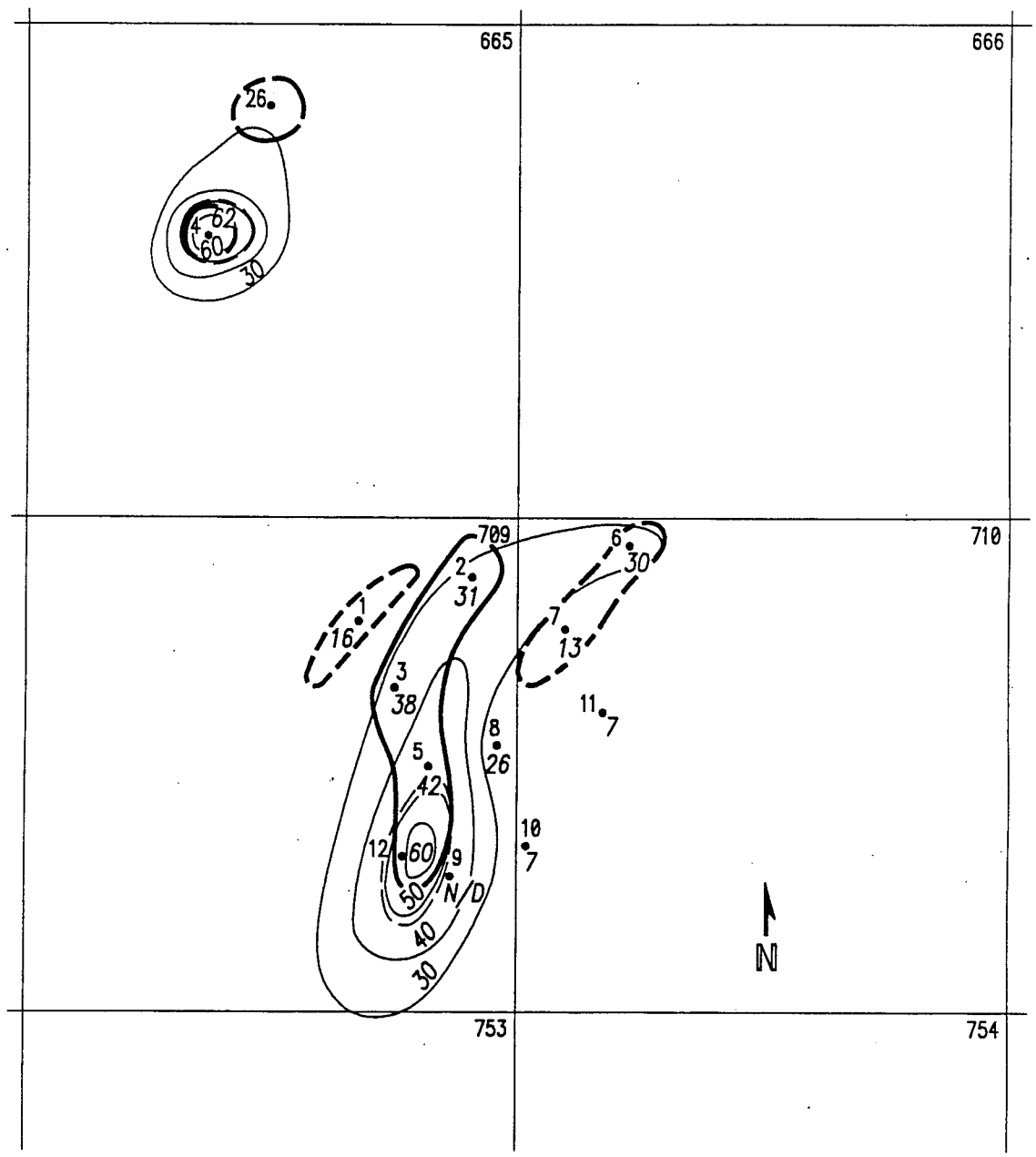
Figure 16:
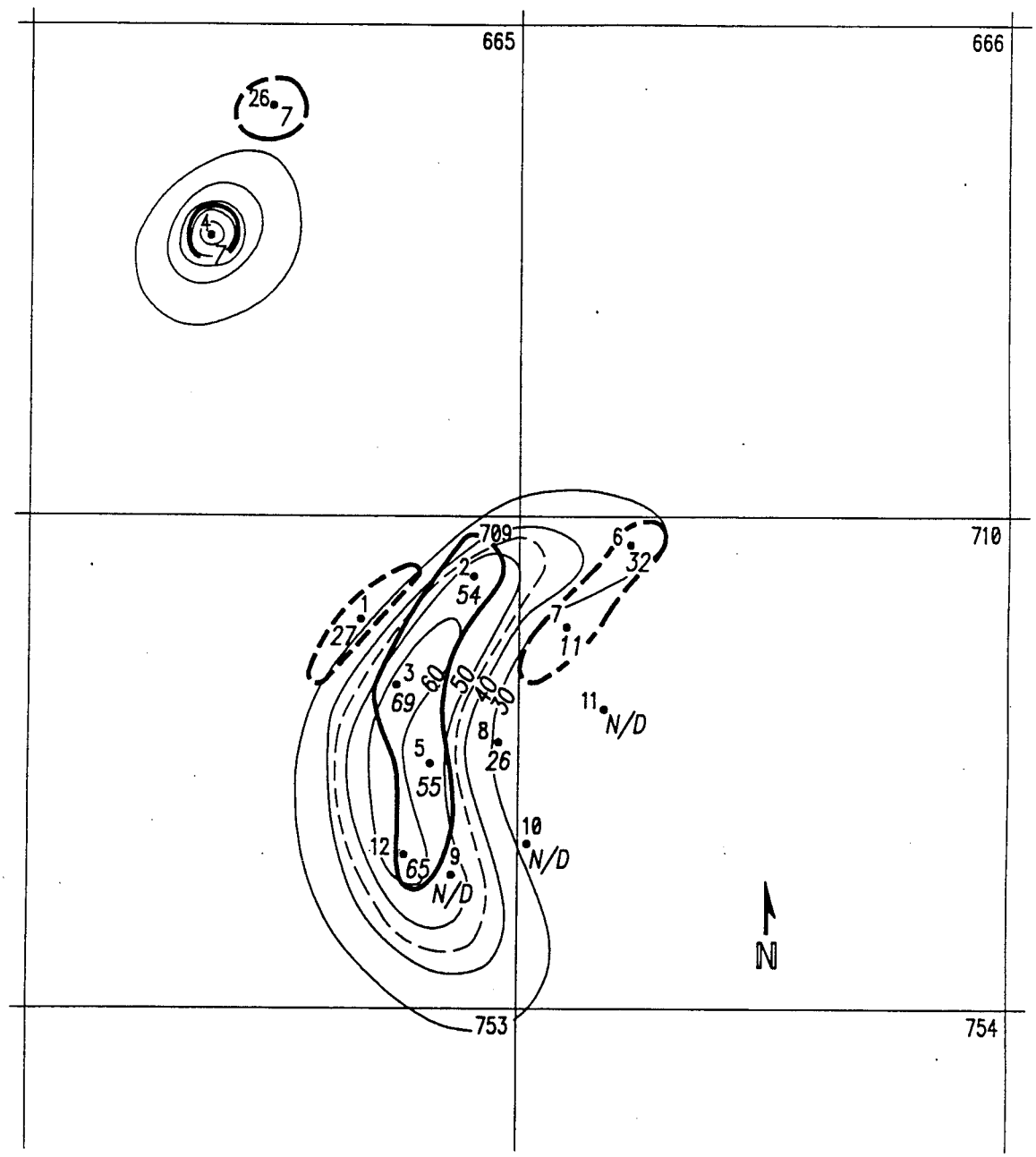
Figure 17:
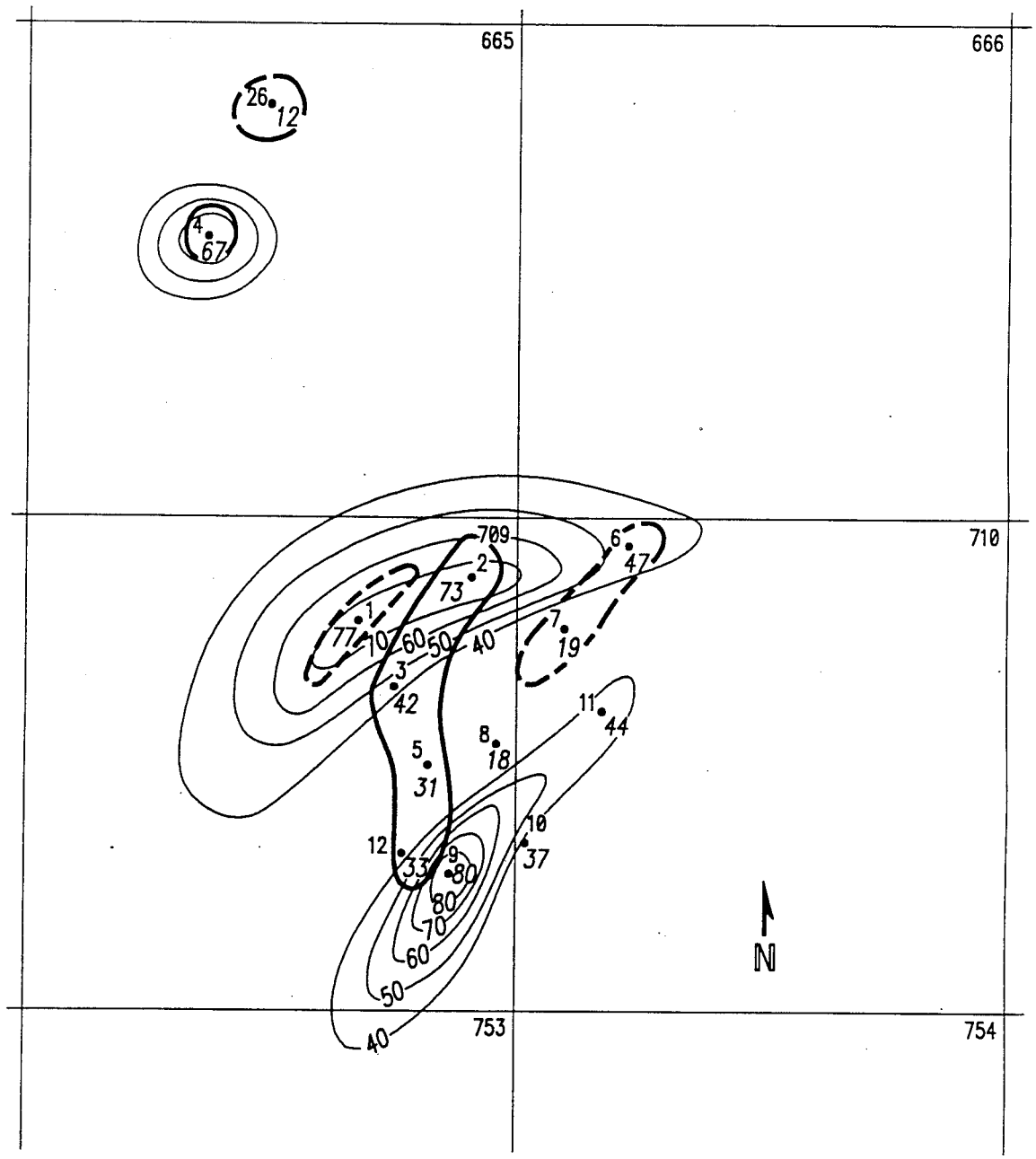
Figure 18:
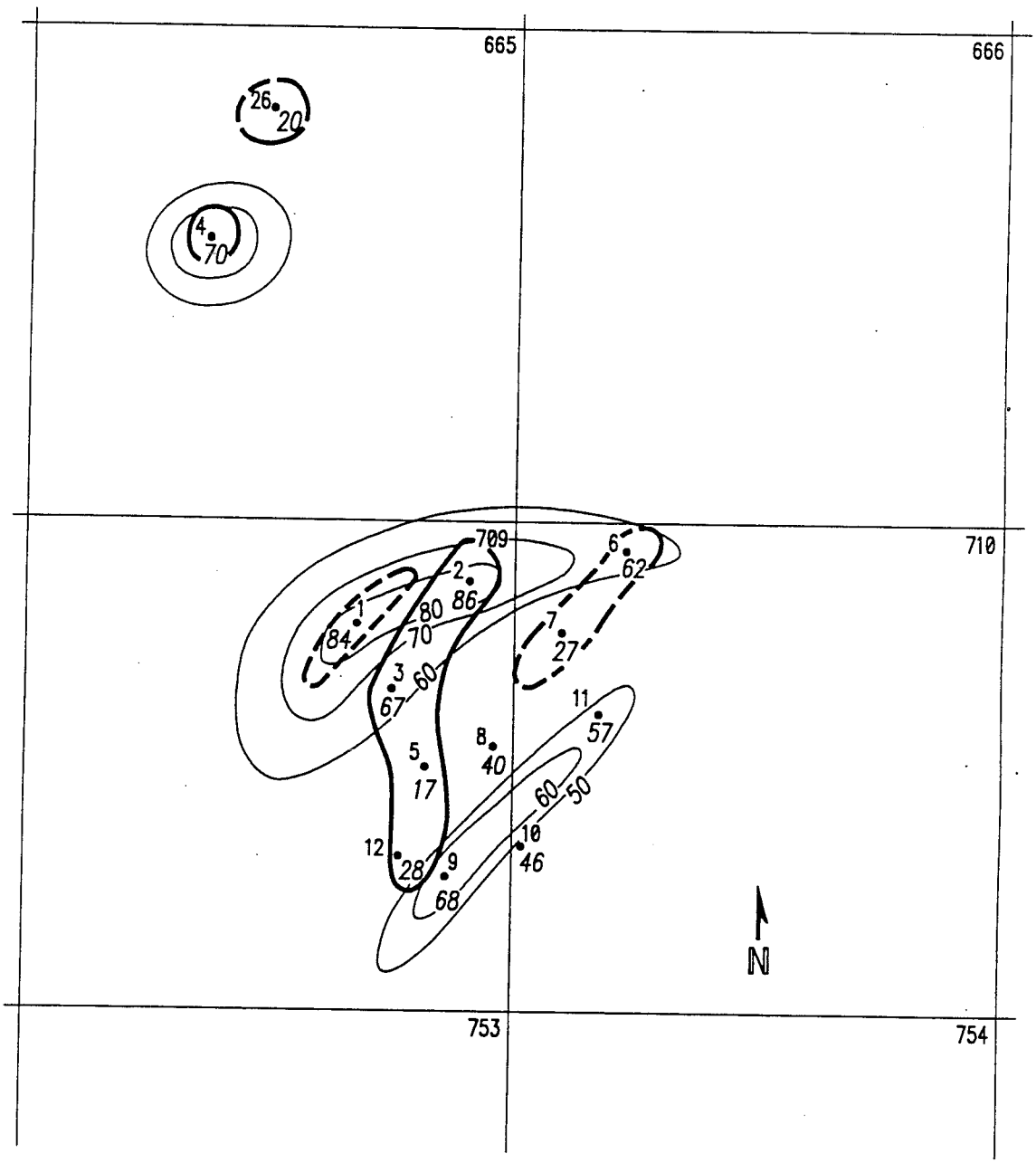
Figure 19:
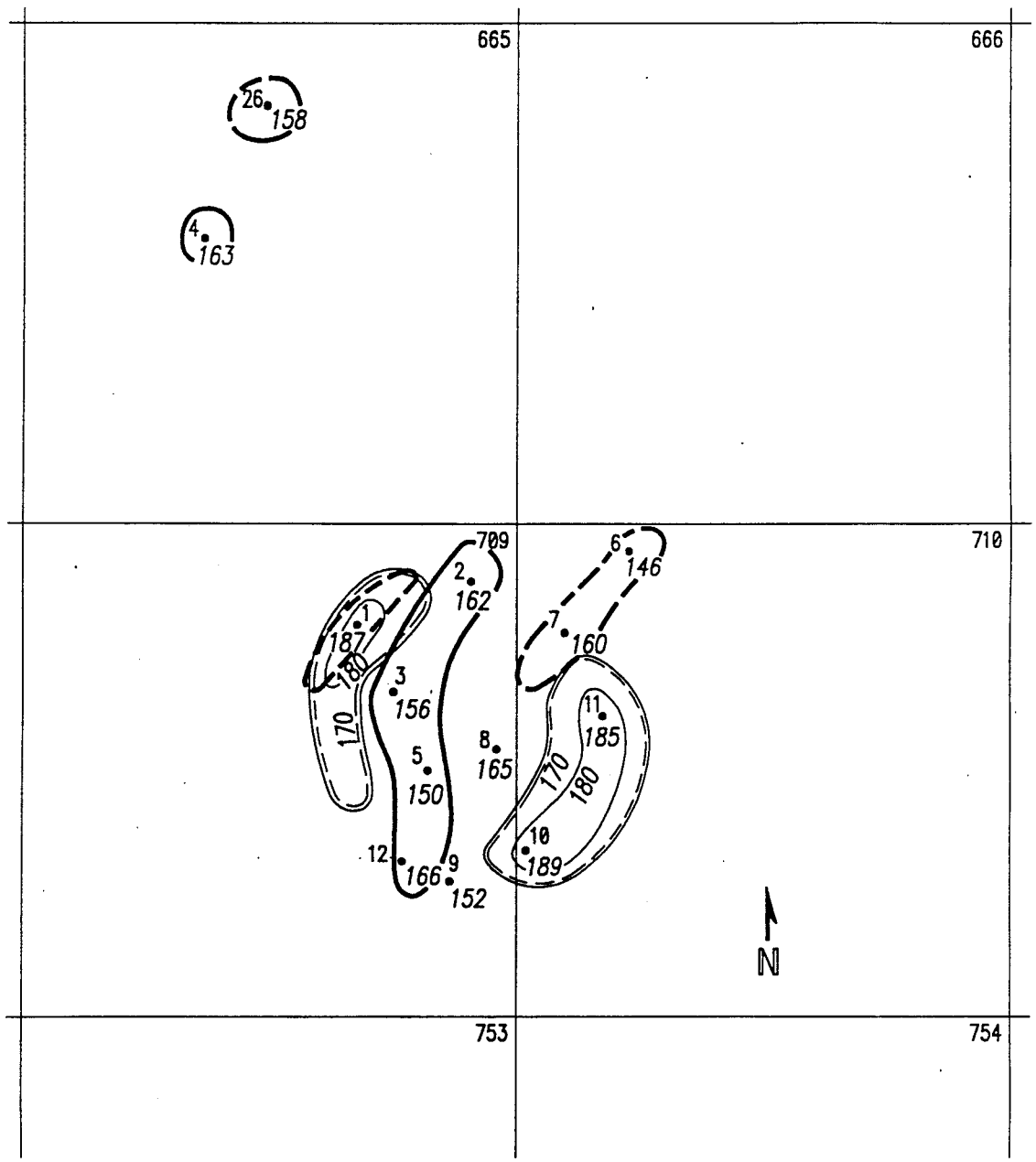
Figure 20:
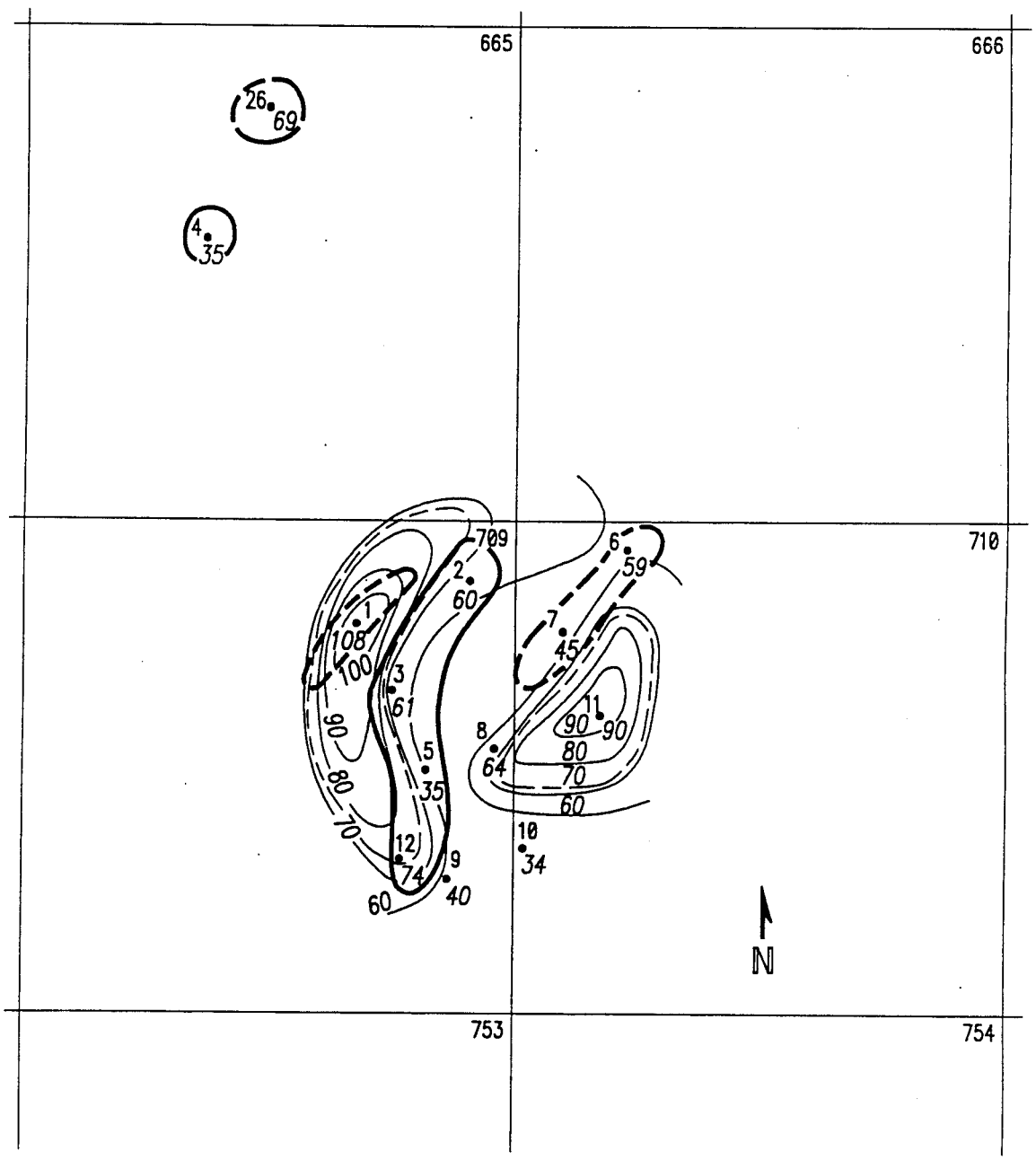
Figure 21:
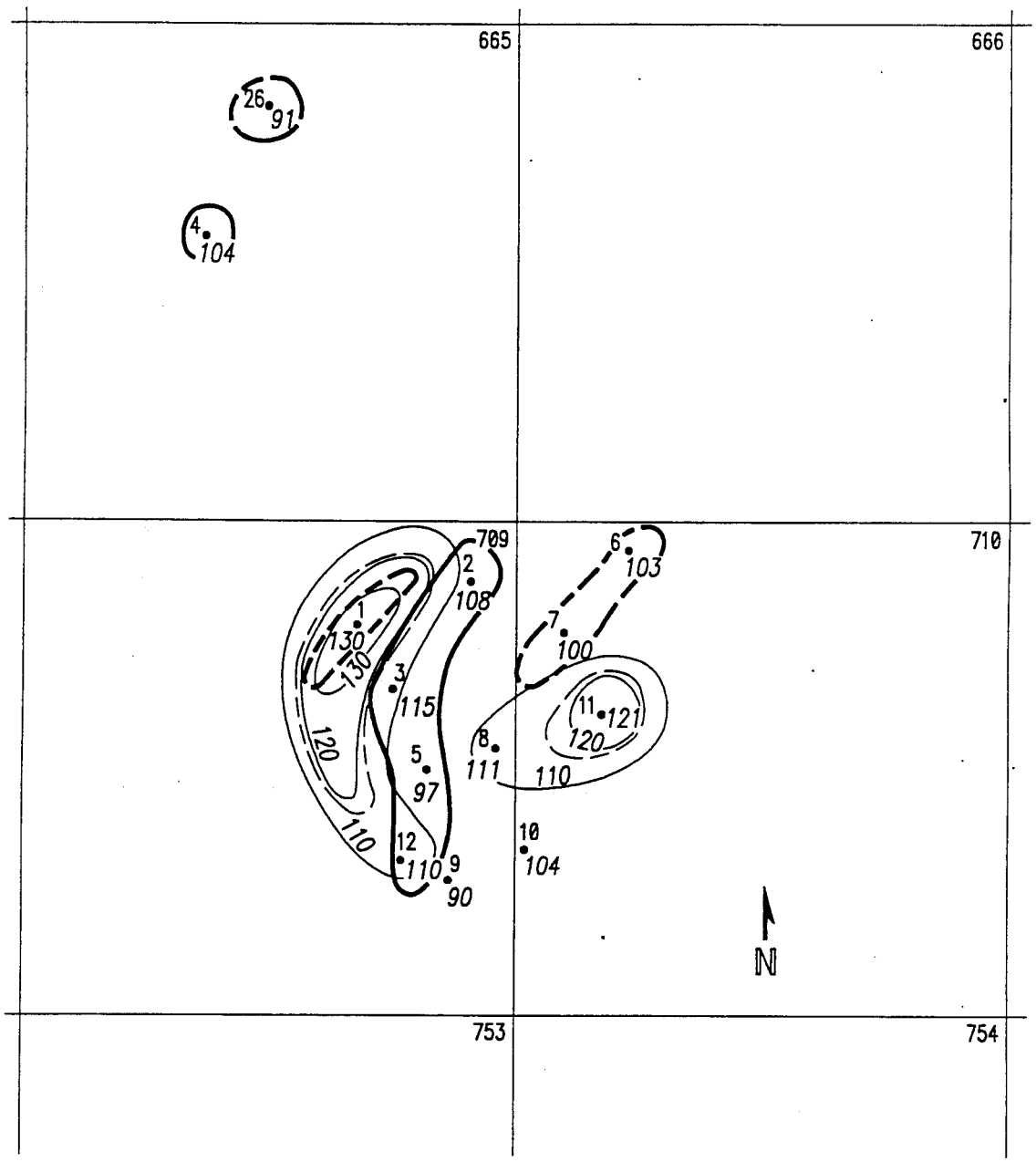

The above described sampling and analytic methods of this invention were applied to subsea petroleum exploration, which is described in more detail in connection with FIGS. 3-21.

This study proceeded in two stages: Stage 1 (FIGS. 3-11) involved a series of assays of a known oil field (MC 486, 487, 530, 531) to correlate the techniques of fast geomicrobial sensitivity assay as described herein to develop tolerance contour maps as a test of the truth of the principles of this invention; and Stage 2 (FIGS. 12-21) involved a second series of assays to first develop tolerance contours in an undrilled raw prospect (MC 665, 666, 709, 710), then target a general area in which to drill, followed by confirming a well site in the general target area by seismic stratigraphic studies, and finally drilling and discovering petroleum (oil and gas) thereby proving that the geomicrobial tolerance/sensitivity assay techniques of this invention are fast, cheap and useful exploration tools.

FIGS. 3 through 11 illustrate by way of example the distribution of metals and metal tolerant microbial communities in the MC 486-531 area, offshore Louisiana, in the Gulf of Mexico. These FIGS. 3-11 (and the others which follow) show: 1) sample number and locations; 2) the percentage of the total population which survives metal and/or hydrocarbon inoculation (FIGS. 1-8); 3) the total concentration of metal present in the sample (FIGS. 9-11); 4) contours depicting aerial (lateral) variance of the raw data (light line); 5) contours depicting either the mean (x) or mean plus one standard deviation (x+1γ) (light dashed line); and 6) the results of conventional SASS Institute multivariate statistical analysis of the raw data (heavy lines)..

In all cases, the multivariate statistical technique (Factor Analysis) showed a positive correlation in the aerial (lateral geographic) distribution of bacteria demonstrating metal and hydrocarbon tolerance (Factor 1—positive load; heavy solid line), and a positive correlation in the aerial (lateral geographic) distribution of high metal concentrations in the sediment samples (Factor 1—negative load; heavy dashed line).

The metal values in FIGS. 9-11 and 19-21 were determined by inorganic acid digestion of sediment samples followed by conventional inductively coupled plasma (ICP) analysis. V and Co are isomorphous; that is, high V is accompanied by high Co, and low with low. Where microbes do not show tolerance to one metal, e.g. V, they may demonstrate it with respect to the isomorph Co.

These data collectively demonstrate that the highest tolerance levels are not present in areas where the highest metal-in-sediment are found (compare FIGS. 1-6 with 8-11). The bacteria must therefore have been exposed to these metals in some other way. We believe these bacteria were exposed to metals which were chelated to hydrocarbons leaking from the reservoirs known to be present in the subsurface in Blocks 486, 487 530 and 531, which reservoirs were discovered by the 8 drill holes posted on these maps. In light of the extremely low concentrations of the metals we tested in subsurface waters, we consider water migration inadequate as an explanation for the metal flux to which these bacterial communities have apparently been exposed. The hydrocarbon tolerance data which are similarly posted and attached as FIGS. 7 and 8, support our discovery that the metals were chelated to hydrocarbons leaking from the reservoirs.

Since the hydrocarbon tolerance data (FIGS. 7 and 8 pentane and hexane survival) shows contours paralleling the heavy metals (FIGS. 1-6), yet the pentane/hexane incubation is faster (3-10 min vs. 2 hrs. for heavy metals) the methods of this invention may employ the hydrocarbon sensitivity assay alone, or in combination with the heavy metal assay described herein.

FIGS. 12 through 21, illustrate the distribution of metals and metal and hydrocarbon-tolerant microbial communities in the undrilled, raw prospect MC 665-710 area, offshore Louisiana in the Gulf of Mexico. These FIGURES show data similar to that just outlined for the known MC 486-531 area and lead to identical interpretive conclusions. They are noteworthy, however, in that these conclusions were reached prior to any drilling in the area. A well was subsequently drilled (see FIG. 12), the small rectangle in Block 709 to the left of the central intersection of the four blocks being the surface entry point, and the symbol "B.H.L." the pay zone location at a true vertical depth (TVD) of 10,343' below surface. The precise choice of drilling point was made based on subsurface seismic analysis. The displacement of the metal/hydrocarbon contours relative to seismic analysis drilling point showing the elongated target zone somewhat below and to the right of the hole is due to seepage drift through intervening formations. A discovery was logged, thereby verifying the utility of the exploration techniques of this invention.

It should be understood that various modifications within the scope of this invention can be made by one of ordinary skill in the art without departing from the spirit thereof. We therefore wish our invention to be defined by the scope of the appended claims as the prior art will permit, and in view of the specification if need be.

REFERENCES

Albright, L. J., Wentworth, J. W., and Wilson, E. M. (1972) Technique for measuring metallic salt effects upon the indigenous heterotrophic microflora of a natural water. Water Res. 6, 1589-1596.

Babich, H., and Stotzky, G. (1980) Environmental factors that influence the toxicity of heavy metal and gaseous pollutants to microorganisms. Crit. Rev. Microbiol. 8, 99-146.

Bell, C.R., Holder-Franklin, M.A., and Franklin, M. (1980) Heterotrophic bacteria in two Canadian rivers. I. Seasonal variations in the predominant bacterial populations. Water Res. 14, 449-460.

Bopp, L. H., Chakrabarty, A.M., and Ehrlich, H. L. (1983) Chromate resistance plasmid in Pseudomonas fluorescens. J. Bacteriol. 155, 1105-1109.

Chen, C-M., Mobley, H. L. T., and Rosen, B. P. (1985) Separate resistances to arsenate and arsenite (antimonate) encoded by the arsenical resistance operon of R factor R773. J. Bacteriol. 161, 158-763.

Costerton, J. W., and Irvin, R. T. (1981) The bacterial glycocalyx in nature and disease. Ann. Rev. Microbiol. 35, 299-324.

Crawford, R. D. (1913) Geology and ore deposits of the Monarch and Tomichi districts, Colorado. Colo. Geol. Survey Bull. 4.

Crawford, R. D., and Worcester, P. G. (1916) Geology and ore deposits of the Gold Brick district, Colorado. Colo. Geol. Survey Bull. 10.

Dings, McC. G., and Robinson, C. S. (1957) Geology and ore deposits of the Garfield Quadrangle, Colorado. U.S. Geol. Survey Prof. Pap. 289.

El-Shaarawi, A. H., Esterby, S. R., and Dutka, B. J. (1981) Bacterial density in water determined by Poisson or negative binomial distributions. Appl. Environ. Microbiol. 41, 107–116.

Foster, T. J. (1983) Pasmid-determined resistance to anti-microbial drugs and toxic metal ions in bacteria. Microbiol. Rev. 47, 361–409.

Fry, J. C., and Zia, T. (1982) Viability of heterotrophic bacteria in freshwater. J. Gen. Microbiol. 128, 2841–2850.

Fuhrman, J. A., and Azam, E. (1982) Thymidine incorporation as a measure of heterotrophic bacterioplankton production in marine surface waters: evaluation and field results. Mar. Biol. 66, 109–120.

Gadd, G. M., and Griffiths, A. J. (1978) Microorganisms and heavy metal toxicity. Microb. Ecol. 4, 303–317.

Goulder, R. (1980) Seasonal variations in heterotrophic activity and population density of planktonic bacteria in a clean river. J. Ecol. 68, 349–363.

Haack, T. K., and McFeters, G. A. (1982) Microbial dynamics of an epilithic mat community in a high alpine stream. Appl. Environ. Microbiol. 43, 702–707.

Haefeli, C., Franklin, C., and Hardy, K. (1984) Plasmid determined silver resistance in Pseudomonas stutzeri isolated from a silver mine. J. Bacteriol. 158, 389–392.

Houba, C., and Remacie, J. (1980) Composition of the saprophytic bacterial communities in freshwater systems contaminated by heavy metals. Microb. Ecol. 6, 55–69.

Jardim, W. F., and Pearson, H. W. (1985) Copper toxicity to cyanobacteria and its dependence on extracellular ligand concentration and degradation. Microb. Ecol. 11, 139–148.

Jonas, R. B., Gilmour, C.C., Stoner, D. L., Weir, M. M., and Tuttle, J. H. (1984) Comparison of methods to measure acute metal and organometal toxicity to natural aquatic microbial communities. Appl. Environ. Microbiol. 47, 1005–1011.

Jones, J. G. (1972) Studies on freshwater bacteria: association with algae and alkaline phosphatase activity. J. Ecol. 60, 59–75.

Jones, J. G., and Simon, B. M. (1980) Variability in microbiological data from a stratifield eutrophic lake. J. Appl. Bacteriol. 49, 127–135.

Karl, D. M., (1980) Cellular nucleotide measurements and applications in microbial ecology. Microbiol. Rev. 44, 739–796.

Karl, D. M., and Craven, D. B. (1980) Effects of alkaline phosphatase activity on nucleotide measurements in aquatic microbial communities. Appl. Environ. Microbiol. 41, 549–561.

Klein, D. A., and Wu, S. (1974) Stress: a factor to be considered in heterotrophic microorganism enumeration from aquatic environments. Appl. Microbiol. 27, 429–431.

Kosinski, R. J., Singleton, F. L., and Foster, B. G. (1979) Sampling culturable heterotrophs from microcosms: a statistical analysis. Appl. Environ. Microbiol. 39, 906–910.

Laegreid, M., Alstad, J., Klaveness, D., and Seip, H. M. (1983) Seasonal variation of cadmium toxicity toward the alga Selenastrum capricornutum Printz in two lakes with different humus content. Environ. Sci. Technol. 17, 357–361.

Michaels, G. B., and Riese, W. C. (1986) Microbiological exploration for mineral deposits: a new technique. Appl. Geochem. 1, 103–109.

Reichardt, W., Overbeck, J., and Steubing, L. (1967) Free dissolved enzymes in lake waters. Nature 216, 1345–1347.

Robinson, J. B., and O. H. Tuovinen. 1984. Mechanisms of microbial resistance and detoxification of mercury and organomercurial compounds: physiological, biochemical, and genetic analyses. Microbiol. Rev. 48, 95–148.

Silver, S. (1981) Mechanisms of plasmid-determined heavy metal resistances. In Molecular Biology, Pathogenicity, and Ecology of Bacterial Plasmids (eds. S. B. Levy, R. C. Clowes and E. L. Koenig). Plenum Press.

Sjogren, R. E., and Port, J. (1981) Heavy metal-antibiotic resistant bacteria in a lake recreational area. Water Air Soil Pollut. 15, 29–44.

Summers, A. O. (1984) Genetic adaptations involving heavy metals, In Current Perspectives in Microbial Ecology (eds. M. J. Klug and C. A. Reddy). American Society for Microbiology.

Timoney, J. F., Port, J., Giles, J., and Spanier, J. (1978) Heavy-metal and antibiotic resistancee in the bacterial flora of sediments of New York Bight, Appl. Environ. Microbiol. 36, 465–472.

Varma, M. M., Thomas, W. A., and Prasad, C. (1976) Resistance to inorganic salts and antibiotics among sewage-borne Enterobacteriaceae and Achromobacteriaceae. J. Appl. Bacteriol. 41, 347–349.

We claim:

1. Petroleum exploration method comprising in sequence, the steps of:

a) obtaining, at least one sample containing ambient microorganism population from an area of potential petroleum interest and recording the source location of said sample; said sample being selected from the group consisting of soil from a B-soil horizon, and subsea sediment obtained below a depth of about 0.5 meters below the surface of the seabed;

b) dividing said sample into at least two aliquots;

c) preparing the first of said aliquots as a control, and the second of said aliquots for testing of sensitivity of said microorganism to at least one toxic material selected form the group consisting of a metal, a hydrocarbon, or combinations thereof;

d) testing said microorganism in said second aliquot for relative sensitivity to at least one of said toxic materials by subjecting said aliquot to at least one concentration of said toxic material for a period of time sufficient to determine the microbial survival rate; and e) assaying the remaining live microorganisms in said aliquots for the quantity of ATP or DNA, and correlating said ATP or DNA level determined in said samples to the quantities of microbes resistant to the reference concentration of heavy metal or hydrocarbon in said test sample; and f) correlating the microorganism sensitivity to relative presence or absence of metals or hydrocarbon products, or their relative presence or absence as a pathfinder for petroleum.

2. Petroleum exploration method as in claim 11 which includes the added step of mapping the microorganism sensitivity correlation data on a map of said area of potential petroleum interest.

3. Petroleum exploration method as in claim 1 wherein said assay is selected from at least one of a luminometry assay and a tritiated thymidine assay.

4. Petroleum exploration method as in claim 1 wherein said sample is tested only for hydrocarbon sensitivity, said hydrocarbons being selected from the group consisting of $C_1$-$D_{33}$ hydrocarbons.

5. Petroleum exploration method as in claim 4 wherein said hydrocarbons are selected from the group consisting of $C_1$-$C_{14}$ hydrocarbons.

6. Petroleum exploration method as in claim 5 wherein said hydrocarbons are selected form the group consisting of at least one of pentane, hexane and combinations thereof.

7. Petroleum exploration method as in claim 3 wherein said sample is tested only for hydrocarbon sensitivity, said hydrocarbons being selected from the group consisting of $C_1$-$C_{33}$ hydrocarbons.

8. Petroleum exploration method as in claim 7 wherein said hydrocarbons are selected from the group consisting of $C_1$-$C_{14}$ hydrocarbons.

9. Petroleum exploration method as in claim 8 wherein said hydrocarbons are selected from the group consisting of at least one of pentane, hexane and combinations thereof.

10. Petroleum exploration method as in claim 11 wherein said sample is tested for hydrocarbon sensitivity, said hydrocarbons being selected from the group consisting of $C_1$-$C_{33}$ hydrocarbons, and is tested for metal sensitivity, said metals being selected from the group consisting of Co, Ni, Zn, B, Cr, Cu, F, Fe, Mn, Mo, Se, Sn, V, As, Hg, Cd, Pb, U, Be, Br, Ga, Ba, Ge, Sb, Re, Al, Ti, Sr, Ag, Au and Rb.

11. Petroleum exploration method as in claim 10 wherein said hydrocarbons are selected from the group consisting of $C_1$-$C_{14}$ hydrocarbons and said metals are selected from Co, Ni, Zn, Cr, Sn, V, Cd, Ag, Au, Ti and U.

12. Petroleum exploration method as in claim 11 wherein said hydrocarbons are selected from the group consisting of pentane, hexane and combinations thereof, and said metals are selected from the group consisting of Co, Ni and Zn.

13. Petroleum exploration method as in claim 33 wherein said sample is tested for hydrocarbon sensitivity, said hydrocarbons being selected from the group consisting of $C_1$-$C_{33}$ hydrocarbons, and is tested for metal sensitivity, said metals being selected from the group consisting of Co, Ni, Zn, B, Cr, Cu, F, Fe, Mn, Mo, Se, Sn, V, As, Hg, Cd, Pb, U, Be, Br, Ga, Ba, Ge, Sb, Re, Al, Ti, Sr, Ag, Au and Rb.

14. Petroleum exploration method as in claim 13 wherein said hydrocarbons are selected from the group consisting of $C_1$-$C_{14}$ hydrocarbons and said metals are selected from the group consisting of Co, Ni, Zn, Cr, Sn, V, Cd, Ag, Au, Ti and U.

15. Petroleum exploration method as in claim 14 wherein said hydrocarbons are selected from the group consisting of pentane, hexane and combinations thereof, and said metals are selected from the group consisting of Co, Ni and Zn.

16. Petroleum exploration method as in claim 33 wherein said testing for relative sensitivity includes the steps of:
 a) selecting a sample aliquot on the order of 100 ul;
 b) adjusting the pH thereof into the range of 7-8 as required;
 c) maintaining the temperature at the approximate temperature of microbial habitat in the range of 5-25 degrees C;
 d) incubating the microorganisms in the sample in the presence of metal ions for from 1-3 hours under continuous agitation or in the presence of hydrocarbons for from 3-15 minutes.

17. Petroleum exploration method as in claim 16 wherein said metal ranges in concentration from about 0.001 ug/ml to about 15,000 ug/ml, and said hydrocarbons range in concentration from about 0.001% by volume to 25% by volume.

18. Petroleum exploration method as in claim 2 wherein said steps of correlating sensitivity and mapping include correlating sediment concentration of said toxic materials in the area of said samples.

19. Petroleum exploration method as in claim 2 which includes the step of determining seepage drift of said petroleum by correlating said microbial sensitivity contours to stratigraphic analysis of the area to one or more potential well drilling location.

20. Petroleum exploration method as in claim 1 wherein:
 a) said correlation step f) includes correlation
  i. the sensitivity of the sample microorganism to metals to the sensitivity of the same sample microorganism to hydrocarbon tolerance to determine the sample microorganism tolerance to hydrocarbon chelated metals;
  ii. mapping the location of said sample on a map of said area of potential petroleum interest and identifying each sample with its hydrocarbon chelated metals data.

* * * * *

UNITED STATES PATENT AND TRADEMARK OFFICE
CERTIFICATE OF CORRECTION

PATENT NO. : 5,055,397
DATED : October 8, 1991
INVENTOR(S) : Glenda B. Michaels, et al.

It is certified that error appears in the above-identified patent and that said Letters Patent is hereby corrected as shown below:

Claim 22, Column 18, line 65, delete "Claim 11" and insert ---Claim 1---.

Claim 4, column 19, line 7, delete "$D_{33}$" and insert ---$C_{33}$---.

Claim 10, Column 19, line 27, delete "claim 11" and insert ---claim 1---.

Claim 13, Column 19, line 46, delete "Claim 33" and insert ---Claim 3---.

Claim 16, column 20, line 13, delete "Claim 33" and insert ---claim 3---.

Signed and Sealed this

Fourteenth Day of September, 1993

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,055,397
DATED : October 8, 1991
INVENTOR(S) : Glenda B. Michaels, et al It is certified that error appears in the above-indentified patent and that said Letters Patent is hereby corrected as shown below:

Column 18, line 65, claim 22, delete "Claim 11" and insert —Claim 1—
Column 19, line 7, claim 4, delete "$D_{33}$" and insert —$C_{33}$—

Column 19, line 27, delete "claim 11" and insert —claim 1—
        line 46, delete "Claim 33" and insert —Claim 3—
Column 20, line 13, delete "Claim 33" and insert —claim 3—
        line 42, after "correlation" insert —of— (second occurrence)

This Certificate supersedes Certificate of Correction issued September 14, 1993

Signed and Sealed this

Twelfth Day of October, 1993

Attest:

BRUCE LEHMAN

Attesting Officer     Commissioner of Patents and Trademarks